(12) United States Patent
Nasser-Ghodsi et al.

(10) Patent No.: US 8,765,496 B2
(45) Date of Patent: Jul. 1, 2014

(54) METHODS AND SYSTEMS FOR MEASURING A CHARACTERISTIC OF A SUBSTRATE OR PREPARING A SUBSTRATE FOR ANALYSIS

(75) Inventors: Mehran Nasser-Ghodsi, Hamilton, MA (US); Mark Borowicz, San Jose, CA (US); Dave Bakker, Cupertino, CA (US); Mehdi Vaez-Iravani, Los Gatos, CA (US); Prashant Aji, San Jose, CA (US); Rudy Garcia, Union City, CA (US); Tzu Chin Chuang, Cupertino, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1241 days.

(21) Appl. No.: 12/110,759

(22) Filed: Apr. 28, 2008

(65) Prior Publication Data

US 2008/0264905 A1  Oct. 30, 2008

Related U.S. Application Data

(62) Division of application No. 11/086,048, filed on Mar. 22, 2005, now Pat. No. 7,365,321.

(60) Provisional application No. 60/555,170, filed on Mar. 22, 2004.

(51) Int. Cl.
*H01L 21/00* (2006.01)

(52) U.S. Cl.
USPC .............. 438/12; 438/14; 438/708; 216/59; 216/66

(58) Field of Classification Search
USPC ............ 216/65, 63, 66, 67, 59; 438/708, 709, 438/12, 14, 16, 783; 430/297, 298
See application file for complete search history.

(56) References Cited

U.S. PATENT DOCUMENTS

| 4,559,450 A | 12/1985 | Robinson et al. |
| 4,645,929 A | 2/1987 | Criegern et al. |

(Continued)

FOREIGN PATENT DOCUMENTS

| JP | 08222175 | 8/1996 |
| JP | 08329876 A2 | 12/1996 |

(Continued)

OTHER PUBLICATIONS

International Search Report for PCT/US05/09324 published on Oct. 10, 2005.

(Continued)

*Primary Examiner* — Lan Vinh
(74) *Attorney, Agent, or Firm* — Anne Marie Mewherter

(57) ABSTRACT

Methods and systems for measuring a characteristic of a substrate or preparing a substrate for analysis are provided. One method for measuring a characteristic of a substrate includes removing a portion of a feature on the substrate using an electron beam to expose a cross-sectional profile of a remaining portion of the feature. The feature may be a photoresist feature. The method also includes measuring a characteristic of the cross-sectional profile. A method for preparing a substrate for analysis includes removing a portion of a material on the substrate proximate to a defect using chemical etching in combination with an electron beam. The defect may be a subsurface defect or a partially subsurface defect. Another method for preparing a substrate for analysis includes removing a portion of a material on a substrate proximate to a defect using chemical etching in combination with an electron beam and a light beam.

21 Claims, 9 Drawing Sheets

(56) References Cited

U.S. PATENT DOCUMENTS

| | | | |
|---|---|---|---|
| 4,842,683 A | 6/1989 | Cheng et al. | |
| 4,912,326 A | 3/1990 | Naito | |
| 5,215,619 A | 6/1993 | Cheng et al. | |
| 5,614,060 A | 3/1997 | Hanawa | |
| 5,740,226 A | 4/1998 | Komiya et al. | |
| 5,770,099 A | 6/1998 | Rice et al. | |
| 5,849,136 A | 12/1998 | Mintz et al. | |
| 5,882,165 A | 3/1999 | Maydan et al. | |
| 5,910,011 A | 6/1999 | Cruse | |
| 5,926,690 A | 7/1999 | Toprac et al. | |
| 5,955,244 A | 9/1999 | Duval | |
| 5,976,310 A | 11/1999 | Levy | |
| 6,040,198 A | 3/2000 | Komiya et al. | |
| 6,072,147 A | 6/2000 | Koshiishi et al. | |
| 6,072,178 A | 6/2000 | Mizuno | |
| 6,074,518 A | 6/2000 | Imafuku et al. | |
| 6,078,045 A | 6/2000 | Maul et al. | |
| 6,083,363 A | 7/2000 | Ashtiani et al. | |
| 6,084,679 A | 7/2000 | Steffan et al. | |
| 6,089,181 A | 7/2000 | Svemasa et al. | |
| 6,107,629 A | 8/2000 | Benninghoven et al. | |
| 6,110,287 A | 8/2000 | Arai et al. | |
| 6,335,129 B1 * | 1/2002 | Asano et al. | 430/5 |
| 6,514,866 B2 | 2/2003 | Russell et al. | |
| 6,633,831 B2 | 10/2003 | Nikoonahad et al. | |
| 6,730,237 B2 | 5/2004 | Sievers et al. | |
| 6,787,783 B2 | 9/2004 | Marchman et al. | |
| 6,843,927 B2 * | 1/2005 | Naser-Ghodsi | 216/84 |
| 6,891,171 B1 * | 5/2005 | Hagiwara et al. | 430/5 |
| 6,921,722 B2 | 7/2005 | Ogure et al. | |
| 6,943,350 B2 | 9/2005 | Nasser-Ghodsi | |
| 7,088,852 B1 * | 8/2006 | Bruce et al. | 382/145 |
| 7,109,483 B2 | 9/2006 | Nakasuji et al. | |
| 7,135,676 B2 * | 11/2006 | Nakasuji et al. | 250/310 |
| 7,172,839 B2 * | 2/2007 | Sugiyama et al. | 430/5 |
| 7,220,975 B2 * | 5/2007 | Koike et al. | 250/491.1 |
| 2003/0146485 A1 * | 8/2003 | Ezaki | 257/499 |
| 2004/0048398 A1 * | 3/2004 | Liang et al. | 438/3 |
| 2004/0202944 A1 * | 10/2004 | Yang et al. | 430/5 |
| 2005/0284181 A1 | 12/2005 | Smith et al. | |

FOREIGN PATENT DOCUMENTS

| | | |
|---|---|---|
| JP | Hei 9-22110 | 1/1997 |
| JP | 2715289 | 2/1998 |
| JP | 2001319923 | 11/2001 |

OTHER PUBLICATIONS

Official Action for Japanese Patent Application No. 2007-505058 mailed Sep. 14, 2010.

Notice of Reasons for Refusal for Japanese Patent Application No. 2007-505058 mailed Mar. 29, 2011.

* cited by examiner

METHODS AND SYSTEMS FOR MEASURING A CHARACTERISTIC OF A SUBSTRATE OR PREPARING A SUBSTRATE FOR ANALYSIS

PRIORITY CLAIM

This application is a divisional of U.S. application Ser. No. 11/086,048 entitled "Methods and Systems for Measuring a Characteristic of a Substrate or Preparing a Substrate for Analysis," which claims priority to U.S. Provisional Application No. 60/555,170 entitled "Methods and Systems for Measuring a Characteristic of a Substrate or Preparing a Substrate for Analysis," filed Mar. 22, 2004, which is incorporated by reference as if fully set forth herein.

BACKGROUND OF THE INVENTION

1. Field of the Invention

The present invention generally relates to methods and systems for measuring a characteristic of a substrate or preparing a substrate for analysis. Certain embodiments relate to methods and systems for measuring a characteristic of a substrate or preparing a substrate for analysis that include removing a portion of a material on a substrate.

2. Description of the Related Art

The following descriptions and examples are not admitted to be prior art by virtue of their inclusion within this section.

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Throughout the fabrication process, parameters of features formed on the wafer are measured for process monitoring and control purposes. For example, three-dimensional metrology of the profile of features on a monitor wafer is often performed at various times during the process. In particular, the three-dimensional profile of photoresist features is often measured after a lithography step to determine if the features have parameters that are within the specifications (specs) set for them. If the parameters of the features are within spec, then the lithography step may be performed on product wafers. On the other hand, if the parameters of the features are not within spec, then one or more parameters of the lithography step may be altered. Another monitor wafer may then be exposed in the lithography process, and the measurements described above may be performed until the parameters of the features are within spec.

The term "monitor wafer" is generally defined as a wafer upon which a semiconductor product will not be formed. Instead, monitor wafers are only used to monitor the parameters of one process tool and, therefore, are generally only processed in that one tool. After use, monitor wafers may be recycled or scrapped depending on the process that they were run through. Monitor wafers are particularly used as process monitors when a metrology or inspection process will damage the wafer. In this manner, monitor wafers, instead of product wafers, will be destroyed thereby reducing the costs of metrology or inspection. However, using monitor wafers to monitor and control processes can be relatively expensive if the monitor wafers are so damaged by metrology or inspection that they cannot be reused. In addition, since there may be significant differences between monitor wafers and product wafers (e.g., usually fewer processes are performed on the monitor wafers than the product wafers which can produce significant differences in the wafers), using monitor wafers may not provide results that are as accurate as measurements performed on a product wafer.

As a result, there are advantages to performing metrology and inspection on product wafers. However, as mentioned above, many metrology and inspection processes damage wafers. For example, wafers on which photoresist features are formed are often cleaved (i.e., fractured) through the photoresist features such that cross-sectional profiles of the features on the cleaved samples can be viewed. Since the wafers are fractured, this destructive metrology technique results in scrapped wafers. Another metrology technique involves photoresist feature cross-sectioning uses ion beams. For 193 nm photoresist features and smaller lines, the photoresist features are exposed to a tungsten or platinum deposition to reduce ion beam induced damage. The deposited metal top layer generates stresses on 193 nm photoresist lines thereby resulting in photoresist compression and deformation. This damage is due, at least in part, to the incomplete conformal coating of the substrate during the deposition process, which produces voids between adjacent photoresist features. The resulting cross-section thus loses structural integrity, and sometimes to such a degree that the results are not a viable indicator of the characteristics (e.g., critical dimension) of the features. In addition, in such metrology techniques, the use of gallium or other metallic liquid ion sources produces metal contamination in the front end of the line (FEOL) portion of semiconductor device fabrication. There are, therefore, several disadvantages to the currently used three-dimensional metrology techniques including destroyed and therefore scrapped wafers, metal contamination, and/or deformed photoresist features.

As the dimensions of advanced semiconductor devices continue to shrink, the presence of defects in the semiconductor devices increasingly limits the successful fabrication, or yield, of the semiconductor devices. For example, a scratch formed on a wafer during chemical-mechanical polishing may cause an open circuit or a short circuit in, or complete failure of, one or more semiconductor devices formed in subsequent processing. Because fabrication of a semiconductor device includes many complex process steps, the adverse effects of defects on total yield may increase exponentially if a defect formed on a wafer in one manufacturing process step causes additional defects to be formed on the wafer in subsequent manufacturing process steps.

Accordingly, defect detection or "inspection" of semiconductor wafers is and will continue to be of significant importance in semiconductor development and manufacturing. In addition, the review and analysis of defects is of significant importance such that the cause of defects may be determined and hopefully corrected. The ability to remove device film layers ("de-layer") at select locations in a controllable fashion is critical for defect review and analysis during the device fabrication process. For example, removing a device film layer may allow a better view of a defect, particularly a subsurface or partially subsurface defect. In addition, removing a device film layer may enable analysis of the defect composition to be performed with less interference from the surrounding film layer.

Current techniques for de-layering of a substrate utilize ion beam etching, laser ablative etching, or mechanical abrasion using a micro-tip. Focused ion beam etching utilizes gallium ions to stimulate etching. Laser ablative techniques utilize lasers to heat the surface of the substrate to cause chemical and thermal reactions that remove the films. The mechanical abrasion technique uses micro-tips to remove the films around the defect.

Of the current techniques, ion beam etching is the most mature technique used to de-layer devices. However, when using an ion beam to stimulate etching, gallium ions from a source are implanted into the films, which can lead to changes in the optical, electrical, and mechanical properties of the etched features and the surrounding areas. The presence of gallium ions on the device can limit further processing of the device and the wafer in the fab, which would result in scrapping the entire wafer. In addition, during focused ion beam etching, the etched material may be deposited in the surrounding areas on the wafer. The other techniques used for de-layering of a substrate also have several disadvantages. For example, the laser ablative technique has low etch selectivity. In addition, the mechanical abrasion method has limited applications to certain large defects and films.

Accordingly, it would be advantageous to develop methods and systems for three-dimensional metrology of features on a substrate and for de-layering a material on a substrate, which do not destroy, contaminate, or deform the substrate or the features.

SUMMARY OF THE INVENTION

The following description of various embodiments of methods and systems for measuring a characteristic of a substrate or preparing a substrate for analysis is not to be construed in any way as limiting the subject matter of the appended claims.

An embodiment of the invention relates to a method for measuring a characteristic of a substrate. In one embodiment, the substrate may include a product wafer. The method includes removing a portion of a feature on the substrate using an electron beam to expose a cross-sectional profile of a remaining portion of the feature. Removing the portion of the feature does not substantially deform the remaining portion of the feature. In addition, the portion of the feature that is removed is substantially confined to an area of the feature illuminated by the electron beam. In one embodiment, the feature may include a photoresist feature.

The method also includes measuring a characteristic of the cross-sectional profile of the remaining portion of the feature. The characteristic of the cross-sectional profile includes a three-dimensional characteristic of the feature. In one embodiment, measuring the characteristic may be performed using the electron beam. In such an embodiment, the method may also include tilting the substrate relative to the electron beam between removing the portion of the feature and measuring the characteristic. In a different embodiment, measuring the characteristic may be performed using a different electron beam. The different electron beam may be arranged at a predetermined tilt position with respect to the substrate. Each of the embodiments of the method described above may include any other step(s) described herein.

Another embodiment relates to a system configured to measure a characteristic of a substrate. In one embodiment, the substrate includes a product wafer. The system includes an electron delivery subsystem configured to deliver one or more electron beams to the substrate. The one or more electron beams can remove a portion of a feature on the substrate to expose a cross-sectional profile of a remaining portion of the feature. In one embodiment, the feature includes a photoresist feature. Removal of the portion of the feature does not substantially deform the remaining portion of the feature. The portion of the feature that is removed is substantially confined to an area of the feature illuminated by the one or more electron beams.

The one or more electron beams can also measure a characteristic of the cross-sectional profile of the remaining portion of the feature. The characteristic of the cross-sectional profile includes a three-dimensional characteristic of the feature. In one embodiment, the system may be configured to tilt the substrate relative to the one or more electron beams between removal of the portion of the feature and measurement of the characteristic. In another embodiment, removal of the portion of the feature is performed using a first of the one or more electron beams. Measurement of the characteristic is performed using a second of the one or more electron beams. The second electron beam may be arranged at a predetermined tilt position with respect to the substrate. Each of the embodiments of the system described above may be further configured as described herein.

An additional embodiment relates to a method for preparing a substrate for analysis. The substrate may include a product wafer. The method includes removing a portion of a material on the substrate proximate to a defect using chemical etching in combination with an electron beam. The defect may include a subsurface defect or a partially subsurface defect. The portion of the material that is removed may have an area that is equal to or less than about 10 µm by about 10 µm. Chemical etching may include exposing the substrate to an etch chemistry. The etch chemistry may include a fluorine-based chemistry, a chlorine-based chemistry, a bromine-based chemistry, or an oxygen-based chemistry. In some embodiments, the method may also include removing a portion of an additional material on the substrate proximate to the defect using the chemical etching in combination with the electron beam. The additional material is different than the material and is formed under the material.

In one embodiment, the method may include analyzing the defect to determine a characteristic of the defect. For example, the method may include analyzing the defect using the electron beam to determine a characteristic of the defect. In another embodiment, the method may include analyzing the defect using an x-ray analysis system to determine a characteristic of the defect. The characteristic of the defect may include a composition of the defect. Each of the embodiments of the method described above may include any other step(s) described herein.

A further embodiment relates to a system configured to prepare a substrate for analysis. In one embodiment, the substrate includes a product wafer. The system includes a chemical delivery subsystem configured to deliver one or more chemicals to a substrate. The system also includes an electron delivery subsystem configured to deliver an electron beam to the substrate. The one or more chemicals in combination with the electron beam remove a portion of a material on the substrate proximate to a defect. The defect may include a subsurface defect or a partially subsurface defect. The portion of the material that is removed may have an area that is equal to or less than about 10 µm by about 10 µm.

In one embodiment, the one or more chemicals may include a fluorine-based chemistry, a chlorine-based chemistry, a bromine-based chemistry, or an oxygen-based chemistry. The one or more chemicals in combination with the electron beam may also remove a portion of an additional material on the substrate proximate to the defect. The additional material is different than the material and is formed under the material.

In some embodiments, the system may also include an analysis subsystem configured to measure a characteristic of the defect. In one embodiment, the electron delivery subsystem may be configured to measure a characteristic of the defect using the electron beam. In this manner, the electron delivery subsystem may also function as an analysis subsystem. In another embodiment, the analysis subsystem may include an x-ray analysis system. In some embodiments, the characteristic of the defect may include a composition. Each of the embodiments of the system described above may be further configured as described herein.

Yet another embodiment relates to a different method for preparing a substrate for analysis. This method includes removing a portion of a material on the substrate proximate to a defect using chemical etching in combination with an electron beam and a light beam. The electron beam is delivered to the substrate coaxially with the light beam. Chemical etching includes exposing the substrate to an etch chemistry. In one embodiment, the etch chemistry may include a fluorine-based chemistry, a chlorine-based chemistry, a bromine-based chemistry, or an oxygen-based chemistry. Removing the portion of the material includes heating the material with the light beam. In addition, removing the portion of the material includes heating a horizontal surface of the material and not substantially heating a vertical surface of the material. The portion of the material that is removed may have an area that is equal to or less than about 10 μm by about 10 μm.

In one embodiment, the method includes generating the light beam with a laser. In some embodiments, the method may also include removing a portion of an additional material on the substrate proximate to the defect using the chemical etching in combination with the electron beam and the light beam. The additional material is different than the material and is formed under the material. Removing the portion of the material and removing the portion of the additional material include differentially heating the material and the additional material with the light beam.

The defect may include a subsurface defect or a partially subsurface defect. In some embodiments, the material may include a device film. In such an embodiment, removing the portion of the material does not substantially alter an aspect ratio of device features on the substrate. In some embodiments, the method may also include analyzing the defect to determine a characteristic of the defect. In one embodiment, the method may include analyzing the defect using the electron beam to determine a characteristic of the defect. In a different embodiment, the method may include analyzing the defect using an x-ray analysis system to determine a characteristic of the defect. In one embodiment, the characteristic of the defect may include a composition. Each of the embodiments of the method described above may include any other step(s) described herein.

An additional embodiment relates to a different system that is configured to prepare a substrate for analysis. This system includes a chemical delivery subsystem that is configured to deliver one or more chemicals to a substrate. The one or more chemicals may include a fluorine-based chemistry, a chlorine-based chemistry, a bromine-based chemistry, or an oxygen-based chemistry. The system also includes an electron and light delivery subsystem configured to deliver an electron beam to the substrate coaxially with a light beam. The one or more chemicals in combination with the electron beam and the light beam remove a portion of a material on the substrate proximate to a defect.

The defect may include a subsurface defect or a partially subsurface defect. In an embodiment, the material may include a device film. In such an embodiment, the one or more chemicals in combination with the electron beam and the light beam do not substantially alter an aspect ratio of device features on the substrate. The portion of the material that is removed may have an area that is equal to or less than about 10 μm by about 10 μm.

In one embodiment, the electron and light delivery subsystem may include a laser that is configured to generate the light beam. The electron and light delivery subsystem also includes an electron column. The electron column may include an optical window configured to allow the light beam to enter the electron column. In addition, the electron and light delivery subsystem may include a mirror with an aperture formed through the mirror. The electron beam passes through the aperture, and the light beam is reflected from the mirror such that the light beam is coaxial with the electron beam.

The electron and light delivery subsystem is also configured such that the light beam heats the material. In addition, the electron and light delivery subsystem may be configured such that the light beam heats a horizontal surface of the material and does not substantially heat a vertical surface of the material. In some embodiments, the one or more chemicals in combination with the electron beam and the light beam may also remove a portion of an additional material on the substrate proximate to the defect. The additional material is different than the material and is formed under the material. In one such embodiment, the electron and light delivery subsystem may be configured such that the light beam differentially heats the material and the additional material.

In some embodiments, the system may also include an analysis subsystem that is configured to measure a characteristic of the defect. In one embodiment, the electron and light delivery subsystem may be configured to measure a characteristic of the defect using the electron beam. Therefore, the electron and light delivery subsystem may function as an analysis subsystem. In another embodiment, the analysis subsystem may include an x-ray analysis system. The characteristic of the defect may be a composition of the defect. Each of the embodiments of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
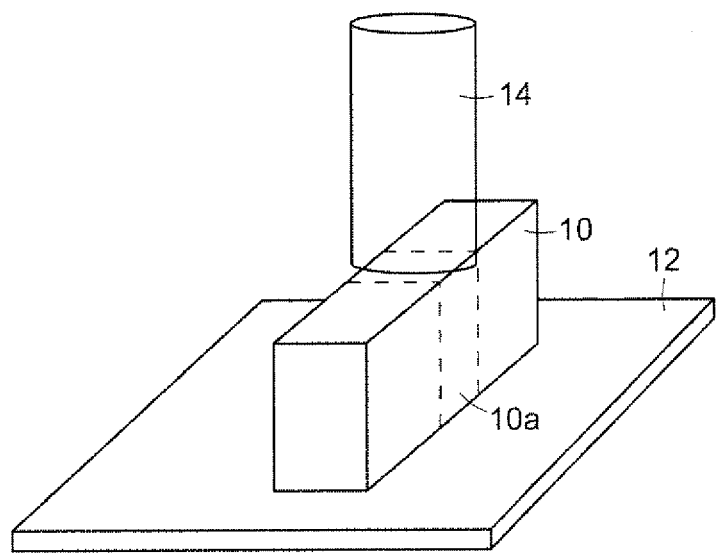
FIG. 1 is a schematic diagram illustrating a partial perspective view of a feature on a substrate, which is exposed to an electron beam.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "substrate" is generally defined as a wafer or a reticle. As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate. Such a wafer is commonly referred to as a "virgin wafer." Alternatively, a wafer may include one or more layers formed upon a substrate. For example, such layers may include, but are not limited to, a resist, a dielectric material, and a conductive material. A resist or a "pholoresist" may include any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose. Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

A "reticle" or a "mask" is generally defined as a substantially transparent substrate having substantially opaque regions formed thereon and configured in a pattern. The substrate may include, for example, a glass material such as quartz. The substantially opaque regions may be formed of a material such as chromium. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source. Many different types of reticles are known in the art, and the term reticle as used herein is intended to encompass all types of reticles.

As used herein, the term "feature" generally refers to any structure formed on a substrate that has some lateral extent in three-dimensions (i.e., a width as well as a height). Examples of features include patterned structures formed on semiconductor wafers. Patterned structures may be formed on semiconductor wafers using any process known in the art (e.g., lithography and etch). The features may be formed of any material known in the art such as a resist, a conductive material, and an insulating material.

Turning now to the drawings, it is noted that FIGS. 1-21 are not drawn to scale. In particular, the scale of some of the elements of the figures is greatly exaggerated to emphasize characteristics of the elements. It is also noted that FIGS. 1-21 are not drawn to the same scale. Elements shown in more than one figure that may be similarly configured have been indicated using the same reference numerals.

Figure 2:
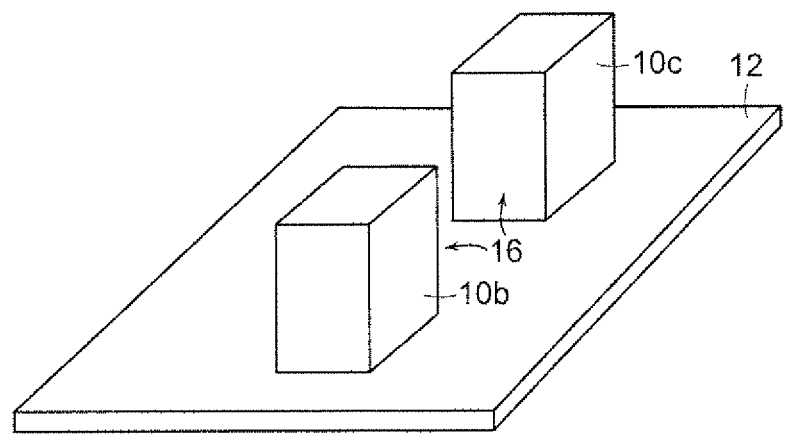
FIG. 2 is a schematic diagram illustrating a partial perspective view of the substrate of FIG. 1 in which a portion of the feature is removed by the electron beam to expose a cross-sectional profile of a remaining portion of the feature.

Turning now to the drawings, FIGS. 1 and 2 illustrate a method for measuring a characteristic of a substrate. As shown in FIG. 1, feature 10 is formed on substrate 12. The feature may be a photoresist feature in one embodiment. However, the feature may be any of the features described above. For example, the feature may be a conductive feature or an insulating feature. Feature 10 is shown as a line. However, it is to be understood that the feature may have any shape. In one embodiment, the substrate may be a product wafer. As such, the feature may be formed in a test area on the product wafer or in a device area on the product wafer. In other words, the feature may be a test feature or a device feature. However, the substrate may include any of the other substrates described above.

As further shown in FIG. 1, the method includes using electron beam 14 to remove portion 10a of feature 10 thereby exposing a cross-sectional profile of a remaining portion of feature 10. In other words, this technique uses an electron beam to remove material from a substrate thereby revealing the orthogonal profile of a feature on the substrate. For example, as shown in FIG. 2, after portion 10a of feature 10 is removed using electron beam 14, cross-sectional profiles 16 of remaining portions 10b and 10c of feature 10 are exposed. As shown in FIGS. 1 and 2, portion 10a of feature 10 that is removed is substantially confined to an area of the feature that is illuminated by electron beam 14. In addition, removing portion 10a of feature 10 does not remove any portion of substrate 12. In this manner, portion 10a of feature 10 can be removed without damaging or destroying substrate 12. In addition, the electron beam will not contaminate the substrate. Therefore, the methods and systems described herein for measuring a characteristic of a substrate are advantageous over other currently used methods and systems since the methods and systems described herein do not contaminate or destroy the substrate.

Figure 3:
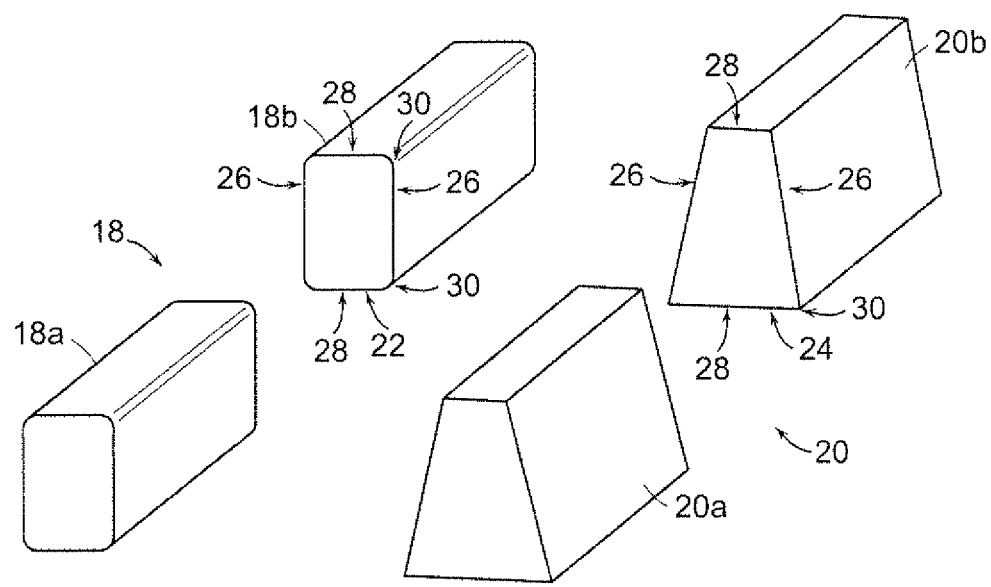
FIG. 3 is a schematic diagram illustrating partial perspective views of other features in which a portion of the features is removed by an electron beam to expose a cross-sectional profile of a remaining portion of the features.

As further shown in FIGS. 1 and 2, removing portion 10a of feature 10 using electron beam 14 does not substantially deform remaining portions 10b and 10c of the feature. In other words, remaining portions 10b and 10c have substantially the same dimensions and three-dimensional profiles as those of feature 10. FIG. 3 also illustrates features having other shapes of which a portion has been removed by the method described herein. As shown in FIG. 3, remaining portions 18a and 18b of feature 18 have substantially the same dimensions and three-dimensional profiles as those of the original feature. In addition, remaining portions 20a and 20b of feature 20 have substantially the same dimensions and three-dimensional profiles as those of the original feature. As shown in FIG. 3, a portion of differently shaped features can be removed as described herein, and the shape of the feature that is being etched by the electron beam will not have any effect on the quality of the remaining portions of the feature.

The quality of the material removal (e.g., horizontal linearity, sidewall orthogonality, material removal rate, etc.) is generally a function of electron beam focus quality, landing energy, etch gas availability, and beam dwell time. Therefore, these parameters of the electron beam can be altered to optimize the material removal and the quality of the remaining portions of the feature. These parameters may also vary depending on, for example, characteristics of the feature (e.g., size and composition) and characteristics of the substrate (e.g., composition, underlying layers, etc.). In this manner, the methods and systems described herein can be used to produce an exposed cross-sectional profile of a feature that is particularly suitable for measurement since the remaining portions of the feature retain the original characteristics of the feature. Therefore, the methods and systems described herein for measuring a characteristic of a substrate are advantageous over other currently used methods and systems since the methods and systems described herein do not cause deformation of the features on the substrate.

The method also includes measuring a characteristic of at least one of the cross-sectional profiles 16 of remaining portions 10b and 10c of feature 10. For example, measuring a characteristic of cross-sectional profiles 16 may be performed using electron beam 14. In such an example, the electron beam may be used to image one of the cross-sectional profiles using a scanning electron microscopy technique. The characteristic that is measured may include a three-dimensional characteristic of the feature (e.g., a critical dimension of the feature, a height of the feature, a sidewall angle or slope of the feature, a three-dimensional profile of the feature, or any other characteristic of the cross-sectional profile that may be measured using a scanning electron microscopy technique). For example, as shown in FIG. 3, three-dimensional characteristics of cross-sectional profiles 22 and 24 of remaining portions 18b and 20b, respectively, that may be measured using scanning electron microscopy include, but are not limited to, critical dimension 26, height 28, and slope 30. Therefore, the methods are particularly useful for three-dimensional metrology of a feature formed on a substrate. In addition, three-dimensional metrology of the feature may be performed while the feature is etched (e.g., using the same electron beam).

If the same electron beam is used to remove the portion of the feature and to measure a characteristic of the cross-sectional profile, the parameters of the subsystem used to deliver the electron beam may be changed between removal and measurement to change one or more characteristics of the electron beam (e.g., energy, focus, etc.). The parameters of the electron beam may vary depending upon, for example, the size of the feature, the composition of the feature, the composition of the substrate, or the composition of the layer of the substrate upon which the feature is formed. Selection of appropriate parameters for removal and measurement will be obvious to one of ordinary skill the art. In particular, the characteristics of the electron beam (and therefore, the parameters of the electron delivery subsystem) may be selected such that the rate at which the portion of the feature is removed enhances the perpendicularity of the exposed cross-sectional profiles. In other words, the characteristics of the electron beam may be selected to avoid under-etch or over-etch of the remaining portions of the feature.

When measuring a characteristic of the cross-sectional profile of the remaining portion of the feature with the same electron beam that is used for removal, the substrate may be tilted relative to the electron beam after the portion of the feature is removed and before the characteristic is measured. In this manner, the electron beam may be arranged at an appropriate viewing angle with respect to the remaining portion of the feature. The substrate may be tilted by altering the position of a stage (not shown) upon which the substrate is disposed between removal of the portion of the feature and measurement. Alternatively, or in addition, the electron beam may be tilted relative to the substrate after the portion of the feature is removed and before measurement such that the electron beam is at an appropriate viewing angle during measurements. The electron beam may be tilted by altering one or more parameters of an electron delivery subsystem that is configured to deliver the electron beam to the substrate.

In a different embodiment, removing the portion of the feature may be performed using one electron beam, and measuring a characteristic of a cross-sectional profile of the feature may be performed using a different electron beam. In such an embodiment, the different electron beam may be arranged at a predetermined tilt position with respect to the substrate. In this manner, after a substrate is placed on a stage coupled to the different electron beam, the position of the stage may not have to be altered before a measurement can be performed.

In one such embodiment, one electron beam may remove a portion of one feature on the substrate while the other electron beam is measuring a characteristic of a cross-sectional profile of a different feature on the substrate. The cross-sectional profile being measured may have been previously exposed using the first electron beam. Therefore, different electron beams may perform different functions (e.g., removal and measurement) on a substrate at the same time. In other words, a substrate may be exposed to two or more electron beams while being disposed on the same stage.

In another example, one electron beam may be used to perform removal and measurement on one feature while another electron beam is performing removal and measurement on another feature. In a different example, one of the electron beams may remove a portion of a feature on one substrate while another electron beam measures a feature on another substrate. Each of the embodiments of the method described above may include any other step(s) described herein.

Figure 4:
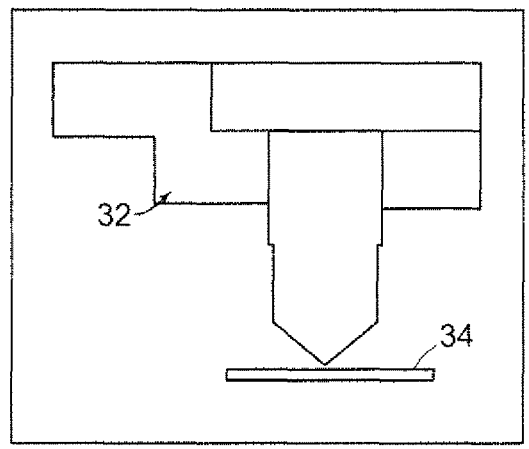
FIGS. 4-7 are schematic diagrams illustrating side views of different embodiments of a system configured to measure a characteristic of a substrate.

Additional embodiments relate to a system configured to measure a characteristic of a substrate according to the method described above. FIG. 4 illustrates an embodiment of one such system. As shown in FIG. 4, the system includes electron delivery subsystem 32. Electron delivery subsystem 32 is configured to deliver an electron beam (not shown) to a substrate (not shown). The system also include stage 34 upon which a substrate may be disposed during removal and measurement. Stage 34 may include any appropriate stage known in the art. The electron delivery subsystem may be configured as an electron column. The electron delivery subsystem may include any appropriate electron column known in the art. The electron delivery subsystem may also include additional components (not shown) coupled to the electron column. The additional components may include, for example, components configured to control the electron column. The system may also include other components such as a processor (not shown) coupled to the electron column and optionally the stage. The processor may be configured to control the electron column and the stage as further described herein.

The electron beam delivered to the substrate by electron delivery subsystem 32 can be used to remove a portion of a feature on the substrate thereby exposing a cross-sectional profile of a remaining portion of the feature as described above. The feature may include a photoresist feature or any of the other features described above. The substrate may be a product wafer or any other substrate described above. As described above, removal of the portion of the feature by the electron beam does not substantially deform the remaining portion of the feature, as shown in FIGS. 2 and 3. In addition, the portion of the feature that is removed is substantially confined to an area of the feature illuminated by the electron beam, as described further above and as shown in FIGS. 1 and 2.

The electron beam delivered to the substrate by electron delivery subsystem 32 can also be used to measure a characteristic of a cross-sectional profile of the remaining portion of the feature. The characteristic may include any three-dimensional characteristic of the feature described above. In one embodiment of the system shown in FIG. 4, the system may be configured to tilt the substrate relative to the electron beam between removal and measurement. For example, the system may include a processor or a controller coupled to stage 34. The processor or controller may be configured to alter a position of stage 34 thereby altering a position of the substrate relative to the electron beam. In this manner, the system may be configured to control the stage such that the substrate may be arranged at an appropriate angle with respect to the electron beam for both removal and measurement.

In another embodiment, the system shown in FIG. 4 may be configured to tilt an electron beam of electron delivery subsystem 32 between removal and measurement. For example, the system may include a processor or a controller coupled to electron delivery subsystem 32. The processor or controller, possibly in combination with one or more components of the electron delivery subsystem, may be configured to alter one or more parameters of the electron column thereby altering a position of the electron beam with respect to the substrate. As such, the system may be configured to control the electron delivery subsystem such that the electron beam may be arranged at an appropriate angle with respect to the substrate for both removal and measurement.

Figure 5:
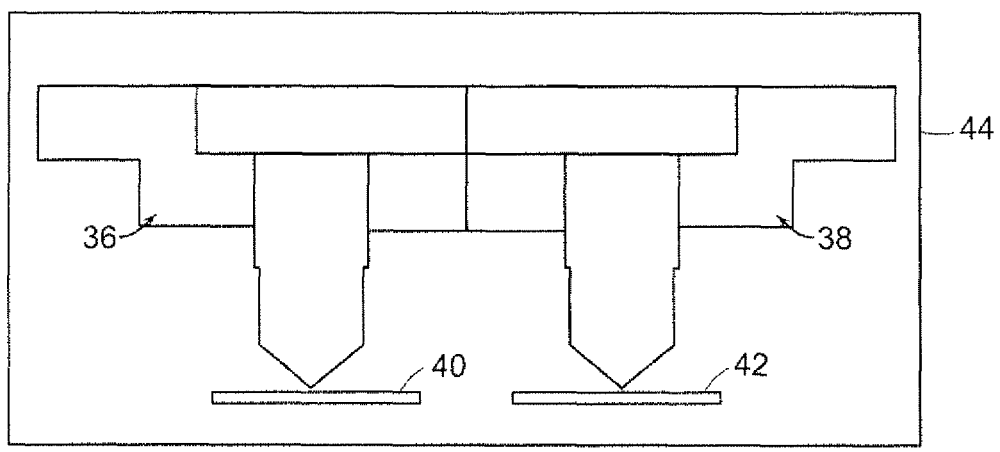
Figure 6:
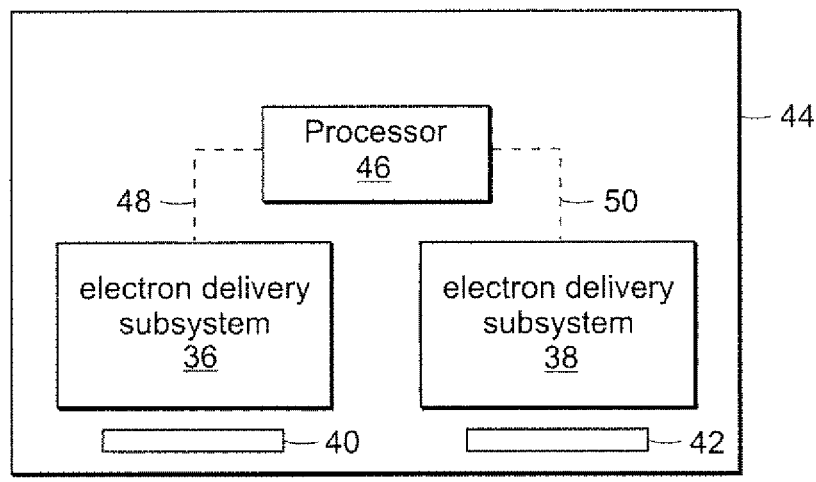

FIG. 5 illustrates another embodiment of a system configured to measure a characteristic of a substrate. In this embodiment, the system includes two electron delivery subsystems 36 and 38. Each of the electron delivery subsystems is configured to deliver an electron beam to a substrate (not shown). For example, electron delivery subsystem 36 is configured to deliver an electron beam (not shown) to a substrate that is disposed on stage 40, and electron delivery subsystem 38 is configured to deliver an electron beam (not shown) to a substrate that is disposed on stage 42. Stages 40 and 42 may include any appropriate stages known in the art. In addition, stages 40 and 42 may be the same or different types of stages.

Each of the electron delivery subsystems may be generally configured as an electron column. The electron delivery subsystems may include any appropriate electron columns known in the art. In addition, the electron columns of the two electron delivery subsystems may be configured similarly or differently. The electron delivery subsystems may also include additional components (not shown) coupled to the electron columns. The additional components may include, for example, components configured to control the electron beams. The system may also include other components such as one or more processors (not shown) coupled to one or more of the electron columns and one or more of the stages. The processor may be configured to control the electron column and the stage as further described herein.

The electron beam delivered to the substrate by electron delivery subsystem 36 can be used for removal as described above. The electron beam delivered to the subsystem by electron delivery subsystem 38 can be used for measurements as described above. In one embodiment of the system shown in FIG. 5, electron delivery subsystem 38 may be configured such that the electron beam that it delivers to the substrate is arranged at a predetermined tilt position with respect to the substrate. In this manner, a position of stage 42 may not have to be substantially altered prior to measurements.

In the system shown in FIG. 5, therefore, one electron delivery subsystem may be used for removal, and another electron delivery subsystem may be used for measurement. In addition, as shown in FIG. 5, each of the electron delivery subsystems is coupled to a different stage. Therefore, after removal of a portion of a feature on a substrate by, for example, an electron beam delivered by electron delivery subsystem 36, a substrate handler (not shown) may remove the substrate from stage 40 and move the substrate to stage 42 such that an electron beam delivered by electron delivery column 38 can measure a characteristic of the feature. Therefore, in one embodiment, the two electron delivery subsystems may be coupled by a common substrate handler. In addition, as shown in FIG. 5, electron delivery columns 36 and 38 may be arranged within one housing 44.

In the embodiment described above, therefore, one electron delivery subsystem may be dedicated to material removal, and the other electron delivery subsystem may be dedicated to measurement. However, it is to be understood that both electron delivery subsystems may also be configured to perform both material removal and measurement, as described above with respect to electron delivery subsystem 32. In either embodiment, the system shown in FIG. 5 may be configured to process two substrates at the same time. For example, one electron delivery subsystem may perform material removal on one feature on one substrate while the other electron delivery subsystem performs a measurement of another feature on another substrate. In another example, one of the electron delivery subsystems can remove a portion of a feature on a substrate and then measure a three-dimensional characteristic of the feature while the other electron delivery subsystem is similarly processing a different substrate.

As described above, the two electron delivery subsystems may be coupled by a common substrate handler or may be arranged within one housing. The two electron delivery subsystems may, however, be coupled in a different manner. For example, in one embodiment shown in FIG. 6, electron delivery subsystem 36 may be coupled to electron delivery subsystem 38 by common processor 46. Processor 46 may be coupled to electron delivery subsystem 36 by transmission medium 48. Processor 46 may also be coupled to electron delivery subsystem 38 by transmission medium 50. Transmission media 48 and 50 may include any appropriate transmission media known in the art and may include "wired" and "wireless" portions. Processor 46 may be configured to perform the various functions described herein. In addition, processor 46 may be configured to receive measurement data from electron delivery subsystem 36 and/or electron delivery subsystem 38. Processor 46 may be configured to process the measurement data using any method known in the art. For example, processor may receive image data from electron delivery subsystem 36 and/or electron delivery subsystem 38. Processor 46 may also use one or more algorithms to extract edges of the feature from the image data and to determine one or more characteristics of the feature from the image data.

Figure 7:
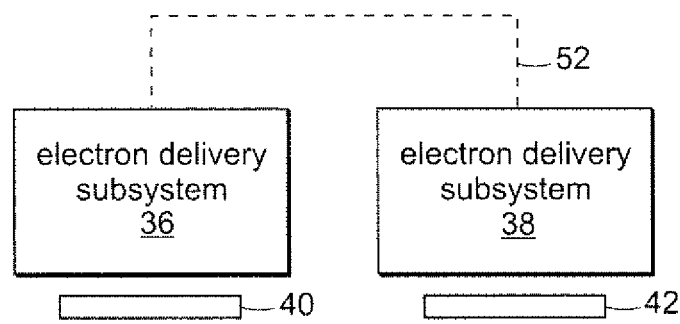

In another embodiment shown in FIG. 7, electron delivery subsystem 36 may be coupled to electron delivery subsystem 38 by transmission medium 52. Transmission medium 52 may include any appropriate transmission medium known in the art and may include "wired" and "wireless" portions. The transmission medium serves as an information link between the two electron delivery subsystems. In addition, electron delivery subsystems 36 and 38 may have their own processors, wafer handlers, housings, power sources, etc. (not shown). As such, each electron delivery subsystem may be configured as a preparation (e.g., material removal) and/or measurement system completely separate from the other subsystem except for the transmission medium. In addition, electron delivery subsystem 36 may be located remotely from electron delivery subsystem 38.

However, regardless of their locations, electron delivery subsystem 36 and electron delivery subsystem 38 may be coupled by transmission medium 52. In one particular embodiment, a processor of electron delivery subsystem 36 may be coupled by transmission medium 52 to a processor of electron delivery subsystem 38. In this manner, measurements and other information may be sent between processors of the subsystems. For example, electron delivery subsystem 36 may send a location of a feature that has been etched as described above to electron delivery subsystem 38. Electron delivery subsystem 38 may then use the information to locate the feature to be measured and then carry out the measurements. The system shown in FIG. 5 may be further configured as described herein. In addition, the processors of subsystems 36 and 38 may be configured as described further herein.

Although the embodiments of the system shown in FIGS. 4-7 include one or two electron delivery subsystems, it is to be understood that in some embodiments a system may include more than two electron delivery subsystems. In this manner, more than two electron beams may be delivered to substrates at the same time for feature etching and/or measurement. In addition, although in the embodiments of the systems shown in FIGS. 4-7 each electron delivery subsystem is coupled to a different stage, it is to be understood that more than one electron delivery subsystem may be coupled to the same stage in some embodiments. In this manner, two or more electron beams may be delivered to one substrate at substantially the same time. As such, feature etching and/or measurement may be carried out at more than one location on the substrate at substantially the same time. The systems shown in FIGS. 4-7 may be further configured as described herein.

Additional methods and systems are described herein that may be used for removing device film layers (de-layering) at selective locations in a controllable fashion. Such de-layering is critical for defect review and analysis during the device fabrication process. As described further above, current techniques for de-layering include ion beam etching, laser ablative etching, and mechanical abrasion using a micro-tip. These techniques have disadvantages such as causing changes in the optical, electrical, and mechanical properties of the etched features and surrounding areas and contamination of the substrate, which effectively destroys the substrate.

Electron beam assisted chemical etching as described further herein has many advantages over these techniques. For example, using an electron beam instead of an ion beam for etching eliminates the ion contamination and the collateral damage that the ion beam causes to surrounding areas. Therefore, the methods and systems described herein are compatible with front end of the line (FEOL) processing and back end of the line (BEOL) processing, and wafers that have been de-layered as described herein can be returned to the process line. In addition, another advantage of electron beam assisted chemical etching is the high degree of etch selectivity and endpoint detection. Selective electron beam assisted chemical etching with fluorine, chlorine, bromine, and oxygen based chemistries has been developed for most of the film layers in DRAM memory devices, logic devices, and photoresist. Furthermore, since the methods and systems described herein have a relatively high throughput, the time in which the root cause of defects can be correctly identified using these methods and systems may be significantly lower than currently used methods and systems.

Figure 8:
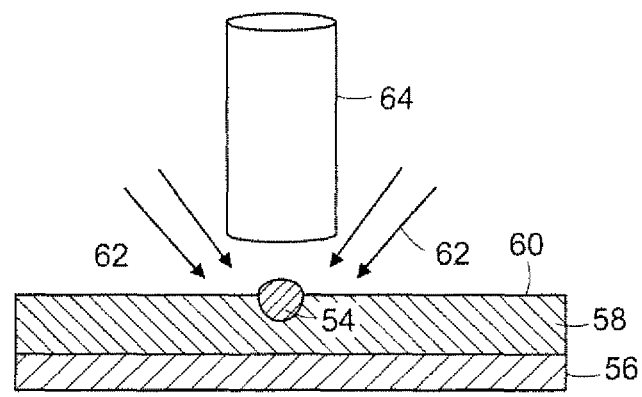
FIG. 8 is a schematic diagram illustrating a partial cross-sectional view of a defect on a substrate, which is exposed to chemical etching in combination with an electron beam.
Figure 9:
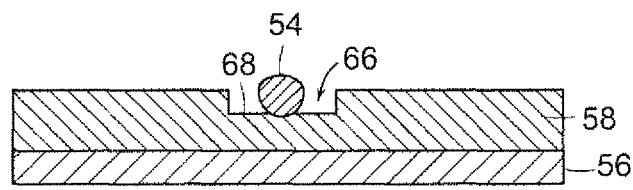
FIG. 9 is a schematic diagram illustrating a partial cross-sectional view of the substrate of FIG. 8 in which a portion of a material on the substrate proximate to the defect is removed.
Figure 10:
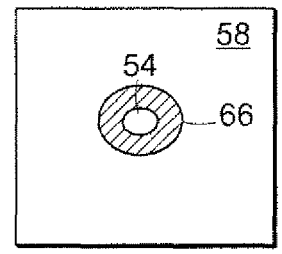
FIG. 10 is a schematic diagram illustrating a partial top view of the substrate of FIG. 9.

FIGS. 8-10 illustrate an embodiment of a method for preparing a substrate for analysis. As shown in FIG. 8, defect 54 is formed on substrate 56. Substrate 56 may include any of the substrates described above. In this example, material 58 is formed on substrate 56. Material 58 may include any material known in the art such as a photoresist, a conductive material, or an insulating material. Although only one material is shown on substrate 56 in FIGS. 8-10, it is to be understood that two or more materials may be formed on the substrates described herein. Some of the materials may be unpatterned as shown in FIGS. 8-10, or may be patterned as described above. As shown in FIG. 8, defect 54 is a partially subsurface defect. In other words, a portion of defect 54 is located below upper surface 60 of material 58. However, the methods and systems described herein may also be performed on substrates that include a completely subsurface defect (such as that shown in FIG. 12 and described further below) or a surface defect (i.e. a defect that does not reside below an upper surface of the substrate). In addition, although defect 54 is shown as a particle defect, it is to be understood that the defect may be any defect known in the art.

As shown in FIG. 8, a portion of material 58 is exposed to chemical etching in combination with electron beam 64. The chemical etching may include exposing substrate 56 to etch chemistry 62. In some embodiments, the etch chemistry may include a fluorine-based chemistry, a chlorine-based chemistry, a bromine-based chemistry, or an oxygen-based chemistry. These etch chemistries may include one or more chemicals. For example, a fluorine-based etch chemistry may include one or more fluorocarbons possibly in combination with other chemicals such as argon. Many such chemistries are known in the art, and the etch chemistry may include any such chemistry. The selection of an etch chemistry may vary depending on, for example, the composition of material 58, the composition of defect 54, and the composition of any other materials on the substrate that might be exposed to the etch chemistry. For example, the etch chemistry is preferably selected such that it does not substantially alter or etch the defect, particularly since the defect is to be analyzed after de-layering as further described herein. In addition, the etch chemistry is preferably selected such that it has good selectivity for material 58 (i.e., it etches material 58 faster than it etches other materials on substrate 56) and, if possible, such that it has good anisotropy (i.e., it etches horizontal surfaces of material 58 faster than it etches vertical surfaces of material 58). Furthermore, the etch chemistry is preferably selected such that it does not substantially etch materials on the substrate other than material 58. In this manner, the etch chemistry may not damage the substrate or other materials or features exposed to the etch chemistry. In addition, the selectivity of the etch can be altered by changing one or more parameters of the electron beam.

As shown in FIG. 9, chemical etching in combination with electron beam 64 removes portion 66 of material 58 proximate to defect 54. As further shown in FIG. 9, the remaining portion of the material proximate to the defect has upper surface 68 that is approximately commensurate with a lower surface of defect 54. However, in other embodiments, the portion of the material proximate the defect may be "over-removed" or "over-etched" such that upper surface 68 is lower than a lowermost surface of the defect. The depth to which the material proximate to the defect is removed may vary depending on, for example, the analysis that is to be performed on the defect.

As shown in FIG. 10, portion 66 of material 58 that is removed proximate defect 54 laterally surrounds defect 54. In this manner, the portion of the material that is removed has an area in which the defect resides. As such, all sides of the defect may be exposed after de-layering such that analysis of the defect may be performed from various angles with respect to the defect. In one embodiment, the portion of the material that is removed has an area that is equal to or less than about 10 µm by about 10 µm. Therefore, the area on the substrate in which material is removed is relatively small, particularly when compared to the amount of material that is typically removed by other de-layering processes. In this manner, the methods described herein may be performed on product wafers since in most instances removing material from such a small area on the product wafer should not adversely affect the product wafer as a whole.

The area of the portion of the material that is removed may vary depending on, for example, the area on the substrate that is illuminated by the electron beam. For example, in the methods and systems described herein, etching takes place only in the presence of etchant gases in combination with the electron beam. In this manner, the diameter of the electron beam, and thereby the area of the removed material, may be altered depending on, for example, the lateral dimensions of the defect, the area that is selected for removal, the analysis that is to be carried out on the defect, the characteristics of the material being removed, and/or the characteristics of the substrate. In one particular example, the area of the material that is removed is preferably kept at a minimum (to avoid damaging or destroying neighboring structures if present) while allowing enough material removal around the defect for analysis to be successfully completed.

Figure 11:
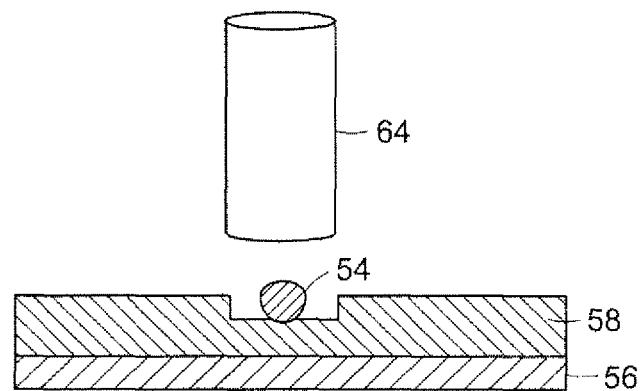
FIG. 11 is a schematic diagram illustrating a partial cross-sectional view of the substrate of FIG. 9 and an electron beam used to determine a characteristic of the defect.

The method may also include analyzing defect 54 to determine a characteristic of the defect. The characteristic of the defect that is determined may include any characteristic that may be of interest such as dimensions (height and width), profile, composition, roughness, etc. Therefore, the characteristic of the defect that is to be determined may determine what analysis is performed on the defect. In one embodiment, analyzing the defect may be performed using an electron beam. In one particular embodiment, as shown in FIG. 11, electron beam 64 that was used to remove portion 66 of material 56 proximate defect 54 may also be used to analyze defect 54. Parameters of the electron beam used to remove the portion of the material may be different than those that are used to analyze the defect. In one such embodiment, the electron beam may be used to image the defect using a technique such as scanning electron microscopy. The image of the defect may then be used for defect review or to determine characteristics of the defect. In another embodiment, electron beam 64 may be used to image the defect as the material is being removed. In this manner, the defect and the de-layering process can be monitored and recorded, possibly in real time, which may provide further information about the defect, the material proximate the defect, and the de-layering process. Such information may also be used to determine an endpoint of the process and/or to optimize the de-layering process.

In another embodiment, the electron beam may be used to determine a composition of the defect using a technique such as energy dispersive x-ray spectroscopy (EDX or EDS) or Auger electron spectroscopy (AES). Once the defect composition has been determined, the de-layering methods described herein may be altered to maximize the selectivity between the defect and the surrounding films. Generally, in the EDX technique, a beam of electrons is directed to a surface of the defect. The defect may emit secondary electrons and a characteristic x-ray in response to the directed beam of electrons. The characteristic x-ray may be detected by a semiconductor x-ray detector and may be subjected to energy analysis. The x-ray spectrum may be analyzed to determine a composition of the defect. Examples of EDX systems and methods are illustrated in U.S. Pat. No. 4,559,450 to Robinson et al., U.S. Pat. No. 6,072,178 to Mizuno, and U.S. Pat. No. 6,084,679 to Steffan et al., and are incorporated by reference as if fully set forth herein.

In another embodiment, an x-ray analysis system (not shown) may be used to determine a characteristic of the defect. For example, a composition of a defect can be determined using a technique such as x-ray photoelectron spectroscopy (XPS or ESCA) or x-ray fluorescence spectrometry (XRF). In another example, an x-ray reflectance (XRR) technique may be used to measure a characteristic of a defect such as a concentration of an element in a defect. Examples of x-ray reflectance methods and systems are illustrated in U.S. Pat. No. 5,740,226 to Komiya et al., U.S. Pat. No. 6,040,198 to Komiya et al., and U.S. Pat. No. 6,633,831 to Nikoonahad et al., which are incorporated by reference as if fully set forth herein. The x-ray analysis system may be configured as described in these patents.

In other embodiments, analysis of the defect may be performed using any other analytical technique known in the art. For example, the defect may be analyzed using secondary ion mass spectroscopy (SIMS). SIMS generally involves removing material from a sample by sputtering ions from the surface of the sample and analyzing the sputtered ions by mass spectrometry. Examples of SIMS techniques are illustrated in U.S. Pat. No. 4,645,929 Criegem et al., U.S. Pat. No. 4,912,326 to Naito, U.S. Pat. No. 6,078,0445 to Maul et al., and U.S. Pat. No. 6,107,629 to Benninghoven et al., and are incorporated by reference as if fully set forth herein. The analysis system may be configured as described in these patents.

Figure 12:
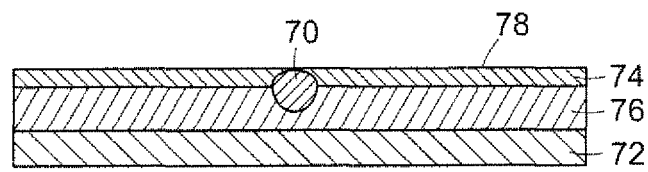
FIG. 12 is a schematic diagram illustrating a partial cross-sectional view of a defect on a substrate.
Figure 13:
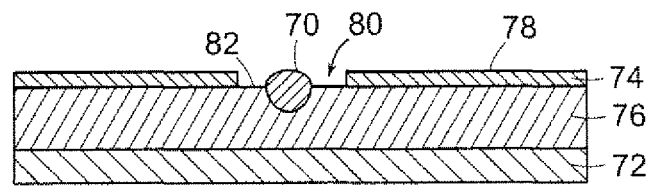
FIG. 13 is a schematic diagram illustrating a partial cross-sectional view of the substrate of FIG. 12 in which a portion of a material on the substrate proximate to the defect is removed.
Figure 14:
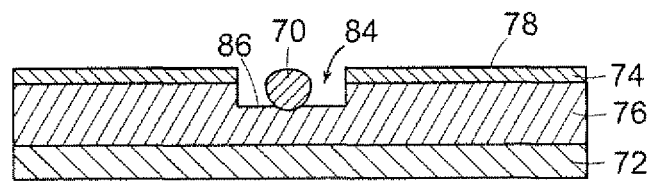
FIG. 14 is a schematic diagram illustrating a partial cross-sectional view of the substrate of FIG. 13 in which a portion of an additional material on the substrate proximate to the defect is removed.

FIGS. 12-14 illustrate another embodiment of a method for preparing a substrate for analysis. As shown in FIG. 12, defect 70 is formed on substrate 72. Substrate 72 may include any of the substrates described above. In this example, materials 74 and 76 are formed on substrate 72. Materials 74 and 76 may be formed on substrate 72 using any process known in the art (e.g., deposition, plating, etc.) or a combination of processes (e.g., deposition and chemical-mechanical polishing).

As shown in FIG. 12, material 76 is formed under material 74. Materials 74 and 76 may include any material known in the art such as a photoresist, a conductive material, or an insulating material. Materials 74 and 76 are different materials. In other words, materials 74 and 76 have different compositions. For example, material 74 may be an insulating material, and material 76 may be a conductive material. Alternatively, material 74 may be one type of insulating material, and material 76 may be a different type of insulating material. Although only two materials are shown formed on substrate 72 in FIGS. 12-14, it is to be understood that many materials may be formed on the substrates described herein. The materials may be unpatterned as shown in FIGS. 12-14, and/or may be patterned as described above.

As shown in FIG. 12, defect 70 is a subsurface defect. In other words, defect 70 is located entirely below upper surface 78 of material 74. However, the methods and systems described herein may also be performed on substrates that include a partially subsurface defect (such as that shown in FIG. 8 and described further above) or a surface defect (i.e., a defect that does not reside below an upper surface of the substrate). Although defect 70 is shown as a particle defect, it is to be understood that the methods and systems described herein may be used for substrates having any type of defect.

As shown in FIG. 13, the method includes removing portion 80 of material 74 proximate to defect 70 using chemical etching in combination with an electron beam (not shown). The chemical etching may include exposing substrate 72 to an etch chemistry (not shown). The etch chemistry may include any of the etch chemistries described herein. In addition, the selectivity of the etch can be altered by changing one or more parameters of the etch chemistry and/or one or more parameters of the electron beam. As shown in FIG. 13, portion 80 of material 74 proximate to the defect may be completely removed to expose upper surface 82 of material 76. As further shown in FIG. 13, removing portion 80 of material 74 has only partially exposed defect 70. Therefore, in some embodiments, as shown in FIG. 14, the method may also include removing portion 84 of material 76 proximate to defect 70 using chemical etching in combination with an electron beam (not shown).

Since materials 74 and 76 are different types of materials, parameters of the chemical etching and the electron beam may be different for removal of the portion of material 74 and for removal of the portion of material 76. For instance, different etch chemistries may be used to remove material 74 and 76. In one example, a fluorine-based etch chemistry may be used to remove material 74, and a chlorine-based etch chemistry may be used to remove material 76. In particular, the etch chemistries may be selected for removal of each of the materials based on the composition and other characteristics of the materials. Preferably, the portions of the different materials are removed in different steps of one etch process that can be carried out in one etch chamber. In addition, the portions of the different materials may be removed in the different steps using the same electron beam. One or more parameters of the electron beam can be altered between the removal steps such that the electron beam may be optimized for removal of both of the different materials. However, it is to be understood that in some instances, removal of the portions of the different materials may be carried out in different etch processes that are performed in different etch chambers possibly in the same etch tool. Obviously, such etch processes would be carried out with different electron beams, which may also have parameters that are optimized for removal of the different materials.

As shown in FIG. 14, the remaining portion of the material proximate to the defect has an upper surface 86 that is approximately commensurate with a lower surface of defect 70. However, in other embodiments, portion 84 of material 76 proximate the defect may be "over-removed" or "over-etched" such that upper surface 86 is lower than a lowermost surface of the defect. The depth to which the material proximate to the defect is removed may vary depending on, for example, the analysis that is to be performed on the defect.

As described further above, portions 80 and 84 of materials 74 and 76 that are removed proximate defect 70 laterally surround defect 70. In this manner, the portions of the materials that are removed have an area in which the defect resides. As such, all sides of the defect may be exposed after the portions of the materials have been removed such that analysis of the defect may be performed from various angles with respect to the defect. In one embodiment, the portions of the materials that are removed have areas that are equal to or less than about 10 μm by about 10 μm. Therefore, the area on the substrate in which materials are removed is relatively small, particularly when compared to the amount of material that is typically removed by other de-layering processes. In this manner, the methods described herein may be performed on product wafers since in most instances removing material from such a small area on the product wafer should not adversely affect the product wafer as a whole. The area of the portions of the materials that are removed may vary depending on, for example, the area on the substrate that is illuminated by the electron beam, as described above.

The method shown in FIGS. 12-14 may also include analyzing defect 70 to determine a characteristic of the defect. The characteristic of the defect that is determined may include any of the characteristics described above. In addition, analysis of the defect may include any of the analysis described above.

Figure 15:
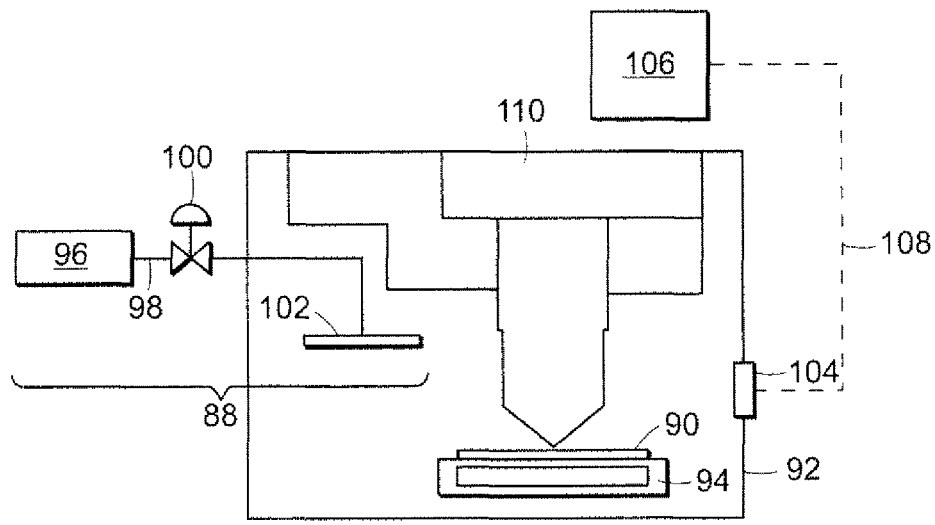
FIG. 15 is a schematic diagram illustrating a side view of an embodiment of a system configured to prepare a substrate for analysis.

FIG. 15 illustrates one embodiment of a system that is configured to prepare a substrate for analysis. The system includes chemical delivery subsystem 88. Chemical delivery subsystem 88 is configured to deliver one or more chemicals (not shown) to substrate 90. In other words, the chemical delivery subsystem is configured to deliver one or more chemicals to process chamber 92 in which substrate 90 is disposed upon stage 94. The one or more chemicals may include any of the chemicals described above. For example, the one or more chemicals may include a fluorine-based chemistry, a chlorine-based chemistry, a bromine-based chemistry, an oxygen-based chemistry, or any other etch chemistry known in the art.

Chemical delivery subsystem 88 may include gas source(s) 96 (only one of which is shown in FIG. 15), tubing 98 coupled to gas source(s) 96, a valve 100 coupled to tubing 98, and dispenser 102. The one or more chemicals may flow from gas source(s) 96 through tubing 98 and valve 100 to dispenser 102. The dispenser allows the one or more chemicals to be released into process chamber 92, preferably in a controllable manner. The gas source(s), tubing, valve, and dispenser may include any such appropriate components known in the art. The chemical delivery subsystem may also include many other components known in the art. In addition, the chemical delivery subsystem may have any configuration known in the art. Additional examples of chemical delivery subsystems are illustrated in U.S. Pat. No. 4,842,683 to Cheng et al., U.S. Pat. No. 5,215,619 to Cheng et al., U.S. Pat. No. 5,614,060 to Hanawa, U.S. Pat. No. 5,770,099 to Rice et al., U.S. Pat. No. 5,882,165 to Maydan et al., U.S. Pat. No. 5,849,136 to Mintz et al., U.S. Pat. No. 5,910,011 to Cruse, U.S. Pat. No. 5,926,690 to Toprac et al., U.S. Pat. No. 5,976,310 to Levy, U.S. Pat. No. 6,072,147 to Koshiishi et al., U.S. Pat. No. 6,074,518 to Imafuku et al., U.S. Pat. No. 6,083,363 to Ashtiani et al., U.S. Pat. No. 6,089,181 to Suemasa et al., U.S. Pat. No. 6,110,287 to Arai et al., and U.S. Pat. No. 6,633,831 to Nikoonahad et al., which are incorporated by reference as if fully set forth herein.

Chemical delivery subsystem 88, process chamber 92 and stage 94 may be further configured as described in these patents. For example, process chamber 92 may include pressure gauge 104. Pressure gauge 104 may be configured to measure a pressure within the process chamber. The pressure gauge may be coupled to processor 106 by transmission medium 108. Transmission medium 108 may include any appropriate transmission medium known in the art. In addition, the transmission medium may include "wired" and "wireless" portions. Processor 106 may be configured to alter one or more parameters of the system depending on the pressure measured by pressure gauge 104. In a similar manner, processor 106 may be coupled to other components of the system (e.g., valve 100) and may be configured to alter other parameters of the system depending on the process being carried out in chamber 92.

The system also includes electron delivery subsystem 110. Electron delivery subsystem 110 is configured to deliver an electron beam (not shown) to substrate 90. The electron delivery subsystem may be further configured as described herein. The one or more chemicals delivered by chemical delivery subsystem 88 in combination with the electron beam delivered by electron delivery subsystem 110 removes a portion of a material on the substrate proximate to the defect. The one or more chemicals in combination with the electron beam may remove a portion of one or more materials as shown in FIGS. 8-10 and 12-14. By-products of the reactions between the material(s) and the one or more chemicals in combination with the electron beam are desorbed from the substrate. The system may include one or more pumps (not shown) that are coupled to the process chamber. The one or more pumps may be configured to remove such by-products from the process chamber thereby reducing the possibility that the by-products may be deposited onto other areas on the substrate. The pump (s) may be any appropriate pumps known in the art.

The defect, the substrate, the material(s), and the portion of the material(s) that are removed may include any of those described above. For example, in one embodiment, the defect may be a subsurface defect or a partially subsurface defect. Alternatively, the defect may be a surface defect. In addition, the portion of the material that is removed may have an area that is equal to or less than about 10 μm by about 10 μm. Furthermore, since the area of the material that is removed is relatively small, the substrate may be a product wafer. However, the substrate may include any other substrates described herein.

In some embodiments, the one or more chemicals delivered by chemical delivery subsystem 88 in combination with the electron beam delivered by electron delivery subsystem 100 may remove a portion of an additional material on the substrate proximate to the defect, as shown in FIGS. 12-14. As further shown in FIGS. 12-14, the additional material (e.g., material 76) is different than the material (e.g., material 74) and is formed under the material.

The system shown in FIG. 15 may also include an analysis subsystem, which is configured to measure a characteristic of the defect on the substrate. The analysis subsystem may be configured to perform one of the analysis techniques described herein. The analysis subsystem may be configured to determine a composition of the defect or any of the other characteristics described herein.

In one embodiment, electron delivery subsystem 110 may be configured to measure a characteristic of the defect using the electron beam. Parameters of the electron beam used for removal may be different than parameters of the electron beam that are used for measurement. The parameters of the electron beam may be altered between removal and measurement by altering one or more parameters of the electron delivery subsystem. The parameter(s) of the electron delivery subsystem may be altered or controlled by processor 106 in some embodiments.

In one embodiment, electron delivery subsystem 110 may be configured to image the defect using a technique such as scanning electron microscopy. In another embodiment, electron delivery subsystem 110 may be used to image the defect as the material is being removed. In this manner, the defect and the de-layering process can be monitored and recorded, which may provide further information about the defect, the material proximate the defect, and the de-layering process. Such information may be used to optimize the de-layering process. In addition, such information may be used to control the de-layering process as it is being carried out (i.e. in real time).

In another example, electron delivery subsystem 110 may be configured to determine a composition of the defect using a technique such as EDX, which is described further above. In this manner, electron delivery subsystem 110 may be configured to function as the analysis subsystem. In a different embodiment, the analysis subsystem may include an x-ray analysis system (not shown) such as those described above or any of those known in the art. The analysis subsystem may be coupled to the system shown in FIG. 15 in any manner. For example, the analysis subsystem and the system shown in FIG. 15 may be disposed in one housing, coupled by a common processor, a common substrate handler, a common power source, a transmission medium, etc. The embodiment of the system shown in FIG. 15 may be further configured as described herein.

In the methods and systems described above, de-layering is accomplished with a combination of electrons and injected etchant gases at the substrate surface. In such embodiments, the de-layering selectivity is largely determined by the etch rates that are obtained by adjusting the etchant gases and the electron beam settings. Although de-layering using electron beam assisted chemical etching is a highly effective de-layering method that offers preferential etching of horizontal surfaces over vertical surfaces mainly from the effect of the incident electron beam, heating of the substrate can further accelerate the etching by accelerating the desorption of reaction by-products at the surface of the substrate. For example, as further described herein, the substrate surfaces can be heated using light to assist the electron and etchant gas reactions.

In one embodiment, a light beam that is coaxially aligned with the electron beam is used to assist in the etch reaction by heating the substrate surface. In particular, the coaxial light beam amplifies the preferential etching of the horizontal surfaces by enhancing the effects of the electron beam on the substrate. For example, by aligning the light beam coaxially with the electron beam, the light beam can preferentially heat the horizontal surfaces. In other words, the coaxial light beam heats the horizontal surfaces on the substrate and does not substantially heat the vertical surfaces. This differential surface heating is used to accelerate the vertical over lateral etching of substrate surfaces. In particular, the etchant gases preferentially etch the horizontal surfaces that are irradiated by both electrons and light. In this manner, the addition of light to the de-layering processes described above can increase the anisotropy of the de-layering processes. Such additional anisotropy may be advantageous since the ability to remove device films while maintaining the original aspect ratio of the device features or any other three-dimensional features is critical in defect review and analysis.

In addition, by selecting the light beam wavelength, different materials on the substrate can be differentially and preferentially heated. For example, the light source may be selected such that the light has a wavelength that can be absorbed by the material that is being removed from the substrate. In this manner, the wavelength may be selected to preferentially heat material(s) that absorb light at that wavelength. As such, the wavelength can be selected to maximize the selectivity between different materials. Such heating may be particularly desirable during de-layering of contacts, capacitors, or other three-dimensional features on the substrate that include two or more materials that are simultaneously being de-layered.

Figure 16:
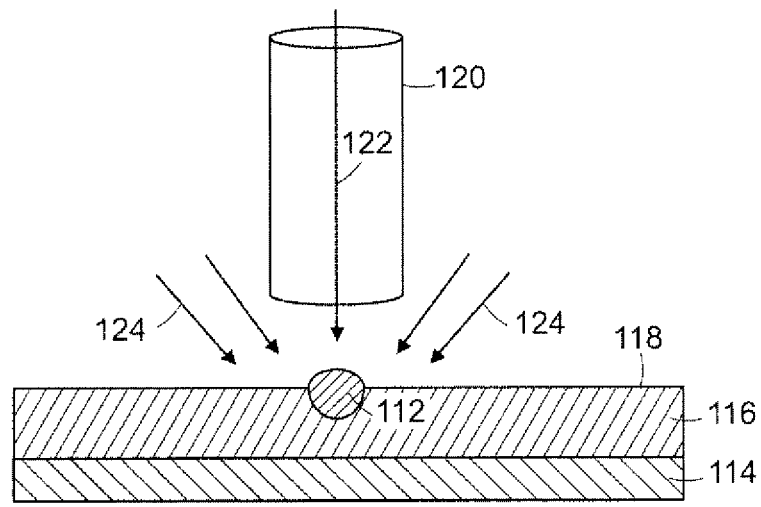
FIG. 16 is a schematic diagram illustrating a partial cross-sectional view of a defect on a substrate, which is exposed to chemical etching in combination with an electron beam and a light beam.
Figure 17:
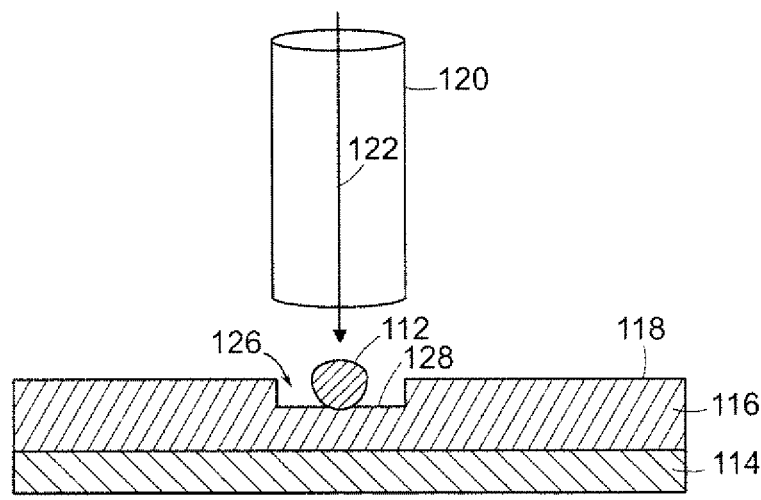
FIG. 17 is a schematic diagram illustrating a partial cross-sectional view of a defect on a substrate, in which a portion of a material on the substrate proximate to the defect has been removed, and an electron beam and a light beam that may be used to determine a characteristic of the defect.

FIGS. 16-17 illustrate one embodiment of a method for preparing a substrate for analysis. As shown in FIG. 16, defect 112 is formed on substrate 114. Substrate 114 may include any of the substrates described above. In this example, material 116 is formed on substrate 114. Material 116 may include any material known in the art such as a photoresist, a conductive material, or an insulating material. Although only one material is shown on substrate 114 in FIGS. 16-17, it is to be understood that many materials may be formed on the substrates described herein. Some of the materials may be unpatterned as shown in FIGS. 16-17, or may be patterned as described above. As shown in FIG. 16, defect 112 is a partially subsurface defect. In other words, a portion of defect 112 is located below upper surface 118 of material 116. However, the methods and systems described herein may also be performed on substrates that include a completely subsurface defect (such as that shown in FIG. 12) or a surface defect. In addition, although defect 112 is shown as a particle defect, it is to be understood that the defect may be any type of defect known in the art.

As shown in FIG. 16, a portion of material 116 is exposed to chemical etching in combination with electron beam 120 and light beam 122. The chemical etching may include exposing substrate 114 to etch chemistry 124. In some embodiments, the etch chemistry may include a fluorine-based chemistry, a chlorine-based chemistry, a bromine-based chemistry, or an oxygen-based chemistry. These etch chemistries may include one or more chemicals. Many such chemistries are known in the art, and the etch chemistry may include any such chemistry.

The selection of an etch chemistry may vary depending on, for example, the composition of material 116, the composition of defect 112, and the composition of any other materials on the substrate that might be exposed to the etch chemistry. For example, the etch chemistry is preferably selected such that it does not substantially alter or etch the defect, particularly since the defect is to be analyzed after de-layering as further described herein. In addition, the etch chemistry is preferably selected such that it has good selectivity for material 116 (i.e., it etches material 116 faster than it etches other materials on substrate 114) and, if possible, such that it has good anisotropy (i.e., it etches horizontal surfaces of material 116 faster than it etches vertical surfaces of material 116). Furthermore, the etch chemistry is preferably selected such that it does not substantially etch materials on the substrate other than material 116. In this manner, the etch chemistry may not damage the substrate or other materials or features exposed to the etch chemistry. In addition, the selectivity of the de-layering process can be altered by changing one or more parameters of the electron beam and/or one or more parameters of the light beam.

As shown in FIG. 16, electron beam 120 is delivered to substrate 114 coaxially with light beam 122. In addition, although the diameter of electron beam 120 is shown in FIG. 16 to be larger than the diameter of light beam 122, it is to be understood that a diameter of light beam 122 may be approximately equal to or greater than the diameter of electron beam 120. Light beam 122 may be generated by a laser (not shown). However, the light beam may be generated by any other appropriate light source known in the art. In general, light sources that are relatively bright at their operating wavelength(s) may be particularly useful in the methods described herein. One example of an appropriate laser is a Q-switched laser in the 100 mW range. Another appropriate laser may be a Ti-sapphire laser. The light source may also be a single wavelength laser or a multiple wavelength laser. In addition, the light beam may be generated using more than one light source. For example, light from several lasers may be combined into an optical train with a combiner. In another example, different light beams may be generated by different lasers, and the light beam that is delivered to the substrate may vary depending on the material being removed. In this manner, not all of the different light beams may be delivered to the substrate at the same time.

The wavelength of light beam 122 will vary depending on the material that is being removed. For example, the wavelength of light beam 122 may be selected such that the light can be absorbed by the material. In this manner, the light beam may heat the material as described above. In addition, the light beam may have one wavelength (e.g., monochromatic light), approximately one wavelength (e.g., near monochromatic light), or more than one wavelength of light (e.g., polychromatic light or broadband light). Examples of appropriate wavelengths include, but are not limited to, about 1054 nm (near infrared), about 527 nm (visible, green), about 350 nm (near ultraviolet), and about 266 nm (ultraviolet). In general, appropriate wavelength(s) may include any wavelength(s) from about 266 nm to about 1054 nm.

If light having different wavelengths is delivered to the substrate at the same time or sequentially, each wavelength of light may heat a specific material on the substrate more than it heats others. Therefore, as material is removed from the substrate, the wavelength of the light that is delivered to the substrate may be changed. For example, after a portion of a material on the substrate is removed, a different material formed under the material may be removed using the chemical etching in combination with the electron beam and the light beam, but with different parameters for at least the light beam. In this manner, removing a portion of more than one material on a substrate may include differentially heating each material with the light beam. In a similar way, when more than one material is being removed from a substrate, parameters of the etch chemistry and/or the electron beam may be changed when different materials are being removed. In this manner, parameters of each component used in the de-layering process may be optimized for removal of the material(s) on the substrate. In addition, parameters of each component used in the de-layering process may be altered to maximize the selectivity of the de-layering process. In particular, the parameters may be altered depending on the composition of the defect, the composition of the material, and in some instances the composition of the substrate. Preferably, the parameters of the etch chemistry, the electron beam, and the light beam used in the de-layering process are optimized to minimize removal of the defect while maximizing removal of the material.

As described further above, light beam 122 preferentially heats material 116 on substrate 114. Heating material 116 with light beam 122 in the presence of etch chemistry 124 and electron beam 120 increases the preferential etching of the horizontal surfaces of material 116. In particular, by delivering light beam 122 to substrate 114 coaxially with electron beam 120, horizontal surfaces of the material can be heated without substantially heating vertical surfaces of the material. In this manner, electron and light beam assisted chemical etching can be substantially anisotropic. As a result, the de-layering methods described herein provide the ability to remove device films while maintaining the original aspect ratio of the device features or any other three-dimensional features on the substrate, which is critical in defect review and analysis.

As shown in FIG. 17, chemical etching in combination with electron beam 120 and light beam 122 removes portion 126 of material 116 proximate to defect 112. As further shown in FIG. 17, the remaining portion of the material proximate to the defect has upper surface 128 that is approximately commensurate with a lower surface of defect 112. However, in other embodiments, the portion of the material proximate the defect may be "over-removed" or "over-etched" such that upper surface 128 is lower than a lowermost surface of defect 112. The depth to which the material is removed may vary depending on, for example, the analysis that is to be performed on the defect.

As described further above, portion 126 of material 116 that is removed proximate defect 112 laterally surrounds defect 112. In this manner, the portion of the material that is removed has an area in which the defect resides. As such, all sides of the defect may be exposed after the portion of the material is removed such that analysis of the defect may be performed from various angles. In one embodiment, the portion of the material that is removed has an area that is equal to or less than about 10 μm by about 10 μm. Therefore, the area on the substrate in which material is removed is relatively small, particularly when compared to the amount of material that is typically removed by other de-layering processes. In this manner, the methods described herein may be performed on product wafers since in most instances removing material from such a small area on the product wafer should not adversely affect the product wafer as a whole.

The area of the portion of the material that is removed may vary depending on, for example, the area on the substrate that is illuminated by the electron beam and the light beam. For example, in the methods and systems described herein, etching takes place only in the presence of etchant gases in combination with the electron beam. In this manner, the diameter of the electron beam may be altered depending on, for example, the lateral dimensions of the defect, the area that is selected for removal, the analysis that is to be carried out on the defect, the characteristics of the material being removed, and/or the characteristics of the substrate. In addition, the area of the portion of the material that is removed may also vary depending on, for example, the area on the substrate that is illuminated by the light beam. The area on the substrate that is illuminated by the light beam may be altered using any method or device known in the art. In one particular example, the area of the material that is removed is preferably kept at a minimum (to avoid damaging or destroying neighboring structures if present) while allowing enough space around the defect for analysis to be successfully completed.

The method may also include analyzing defect 112 to determine a characteristic of the defect. The characteristic of the defect that is determined may include any characteristic that may be of interest such as dimensions (width and height), profile, composition, roughness, etc. Therefore, the characteristic of the defect that is to be determined may determine what analysis is performed on the defect. In one embodiment, analyzing the defect may be performed using an electron beam to determine the characteristic of the defect. In one particular embodiment, as shown in FIG. 17, electron beam 120 that was used for removal may also be used to analyze defect 112. Parameters of the electron beam used for removal may be different than parameters of the electron beam that are used to analyze the defect.

In one such embodiment, electron beam 120 may be used to image the defect using a technique such as scanning electron microscopy. The image of the defect may then be used for defect review or to determine characteristics such as lateral dimensions of the defect. In another embodiment, electron beam 120 may be used to image the defect as the material is being removed. In this manner, the defect and the de-layering process can be monitored and recorded, which may provide further information about the defect, the material proximate the defect, and the de-layering process. The information may be used to monitor and/or control the de-layering process as described further herein. In another embodiment, the electron beam may be used to determine a composition of the defect using a technique such as EDX or AES, as described further above. Once the defect composition has been determined, the de-layering methods described herein may be altered to maximize the selectivity between the defect and the surrounding films.

In another embodiment, an x-ray analysis system (not shown) may be used to determine a characteristic of the defect. For example, a characteristic of a defect such as composition can be determined using a technique such as XPS or XRF. In another example, an XRR technique may be used to measure a characteristic of a defect such as a concentration of an element in the defect. The x-ray analysis system may be further configured as described above. In other embodiments, analysis of the defect may be performed using any other analytical technique known in the art. For example, the defect may be analyzed using SIMS, as described further above.

In other embodiments, light beam 122 may be used to analyze the defect. For example, light beam 122 may be used to image the defect. The image of the defect may then be used to determine one or more characteristics of the defect. The characteristic(s) of the defect that can be determined in this manner may include, but are not limited to, a lateral dimension of the defect, a height of the defect, etc. Parameters of the light beam may be changed between removal and analysis. For example, a wavelength and/or a polarization of the light beam may be changed after de-layering but before analysis of the defect is performed. Other parameters of light beam 122 may be similarly altered between removal and analysis. In another embodiment, light beam 122 may be used to image the defect as the material is being removed. In this manner, the defect and the de-layering process can be monitored and recorded, which may provide further information about the defect, the material proximate the defect, and the de-layering process. This information can be used to monitor and/or control the de-layering process as described further herein. In other embodiments, a different light beam may be used to analyze the defect as described herein. This light beam may or may not be coaxial with electron beam 120.

Figure 18:
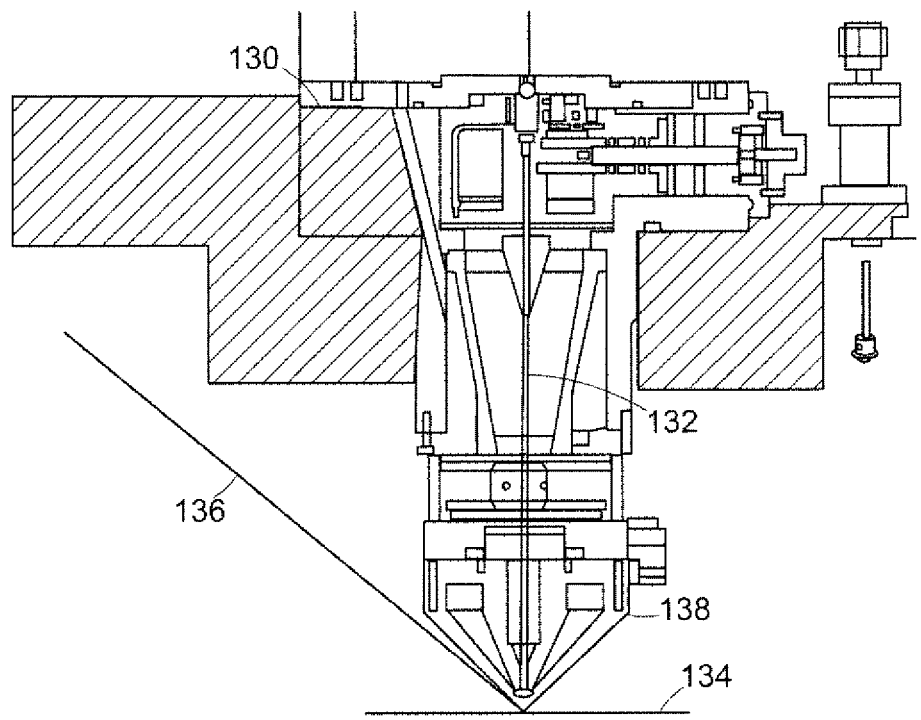
FIG. 18 is a schematic diagram illustrating a partial cross-sectional view of a system configured to prepare a substrate for analysis.

FIG. 18 illustrates one example of a system that is configured to prepare a substrate for analysis. In this example, the system includes electron delivery subsystem 130. Electron delivery subsystem 130 is configured as an electron column. The electron delivery subsystem is configured to deliver electron beam 132 to substrate 134. As shown in FIG. 18, the system is also configured to deliver light beam 136 to substrate 134. Light beam 136 and electron beam 132 are delivered to approximately the same spot on substrate 134.

Figure 19:
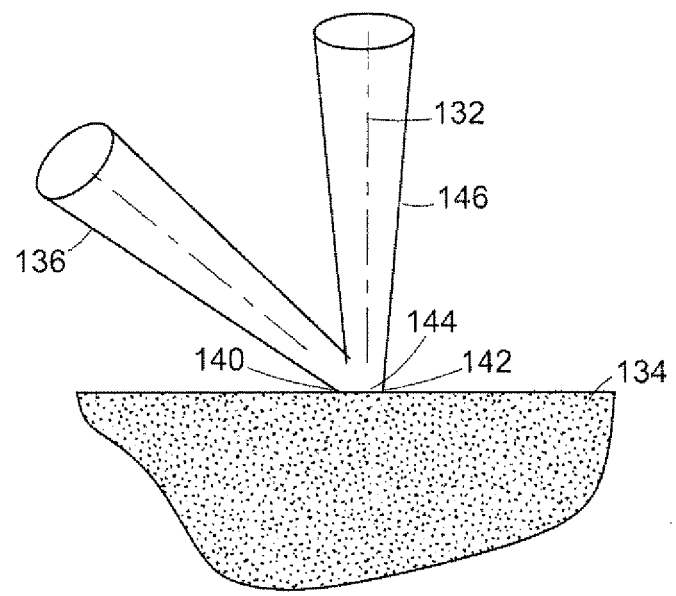
FIG. 19 is a schematic diagram illustrating a side view of focal spots on a substrate by off-axis and coaxial laser delivery.

As shown in FIG. 18, light beam 136 is delivered to the substrate by focusing the beam at a glancing angle that is tangential to the outside edge of objective lens 138 of the electron delivery subsystem. In this manner, the light beam is off-axis with respect to the electron beam. In other words, the light beam is not delivered to the substrate coaxially with the electron beam. This configuration allows the light beam to be focused on the substrate without any modifications to the electron column. However, because the light beam is focused at a glancing angle (about 55° from the vertical), the intersection point of the electron beam focus, the light beam focus and the substrate is critically dependent on the striking distance (i.e., the separation of the objective lens and the substrate). Any change in the working distance would cause the laser beam to overshoot or undershoot the axial point, necessitating a re-alignment of the light beam. In addition, as shown in FIG. 19, because light beam 136 lands on substrate 134 at a glancing angle, focal spot 140 of light beam 136 is an ellipse smeared out in the major diameter by a factor of about 1.74, while focal spot 142 of electron beam 132 is circular. Also, reflectance 144 of the surface at the glancing angle decreases the amount of energy delivered to the process by the light beam.

Delivering the light beam to the substrate coaxially with the electron beam eliminates the problems outlined above. As shown in FIG. 19, when light beam 146 is delivered to substrate 134 coaxially with electron beam 132, the focal spots of both beams are circular. In addition, the focal spot of light beam 146 will be substantially uniform. Therefore, the electron beam focus, the light beam focus, and the substrate will not be critically dependent on the separation of the objective lens and the substrate. In this manner, alignment of the light beam is not critically dependent on the working distance. As such, changes in the working distance will not require re-alignment of light beam 146. Therefore, the systems described further herein will be easier to operate than non-coaxial systems. Furthermore, delivering light beam 146 to substrate 134 at a substantially normal angle will reduce reflectance of the light beam from the surface of the substrate. Consequently, the systems described further herein will have improved delivery of light energy to the de-layering process.

Figure 20:
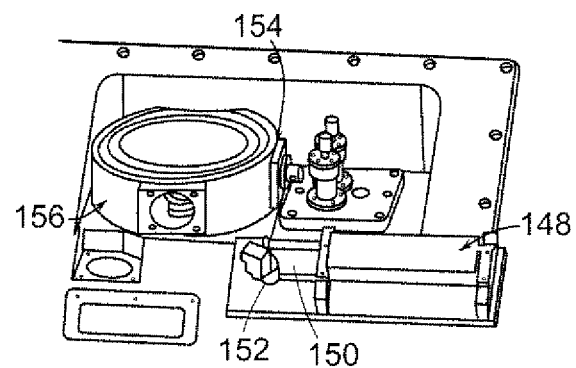
FIG. 20 is a schematic diagram illustrating a perspective top view of one embodiment of a portion of a system configured to prepare a substrate for analysis.
Figure 21:
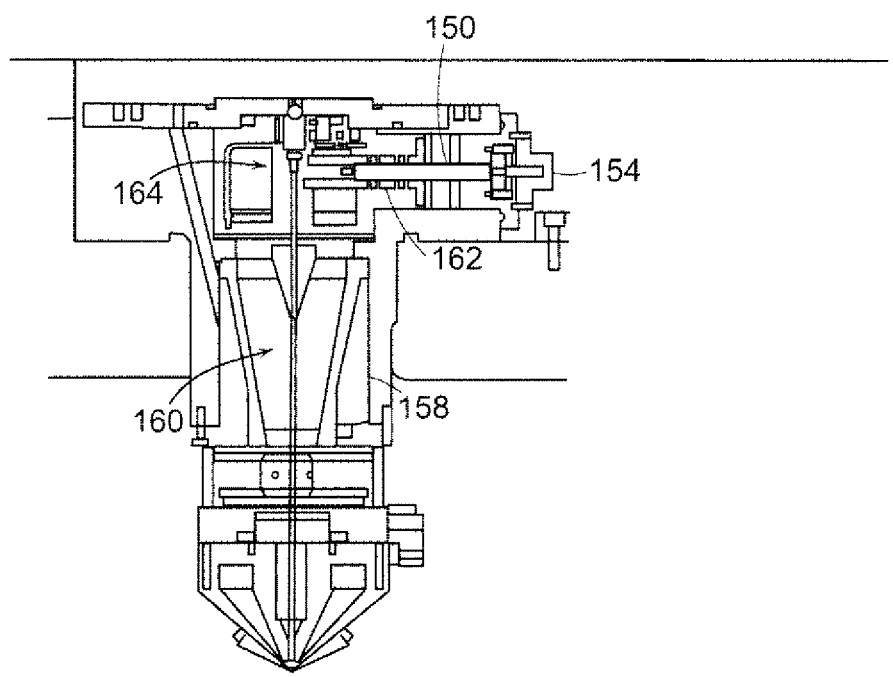
FIG. 21 is a schematic diagram illustrating a partial cross-sectional view of an embodiment of a portion of a system configured to prepare a substrate for analysis.

FIGS. 20 and 21 illustrate one embodiment of an electron and light delivery subsystem that may be included in a system configured to prepare a substrate for analysis. The electron and light delivery subsystem is configured to illuminate the field of view of an electron beam with light or laser energy focused to a relatively small spot diameter. Therefore, the system is configured to enhance the de-layering process by heating the portion of the material that is being removed and to differentially etch different materials. As shown in FIG. 20, the electron and light delivery subsystem includes light source 148. Light source 148 is configured to generate light beam 150. Light beam 150 is directed by optical component 152 to optical window 154 in column base 156 of an electron column of the electron and light delivery subsystem. The optical window may be configured as a vacuum window. The optical window is configured to allow light beam 150 to enter the electron column.

As shown in FIG. 21, electron column 158 is configured to deliver electron beam 160 to a substrate (not shown). After entering electron column 158 through optical window 154, light beam 150 is focused to a spot (e.g., by a simple lens (not shown)), and this image is focused by lens 162 to mirror 164 and eventually to the substrate. Lens 162 may be a long focal length transfer lens or any other appropriate lens known in the art. Light beam 150 is reflected from mirror 164. Mirror 164 may be a 45° metallic mirror. Mirror 164 may also be a convolving laser mirror. Mirror 164 has an aperture (not shown) formed through the mirror. Preferably, the aperture is configured to allow electron beam 160 to pass through the aperture. For example, the aperture may be centered in the mirror and may have a diameter of about 1 mm. In addition, the mirror is preferably placed axially in the electron column with the aperture lined up with the axis of electron beam 160. In this manner, the electron beam can follow its axial path through the electron column and through the aperture in mirror 164. Therefore, after being reflected from mirror 164, light beam 150 will be coaxial with electron beam 160. In this manner, the electron and light delivery subsystem is configured to deliver electron beam 160 to the substrate coaxially with light beam 150. Although there will be a slight loss of light beam power (e.g., about 5%) due to the aperture in the center of the mirror, such a loss is acceptable and will not diminish the functionality of the electron and light delivery subsystem.

The electron and light delivery subsystem shown in FIGS. 20 and 21 may be included in a system along with a chemical delivery subsystem (not shown) that is configured to delivery one or more chemicals to a substrate. The chemical delivery subsystem may be configured as described above. The one or more chemicals in combination with electron beam 160 and light beam 150 remove a portion of a material on the substrate proximate to a defect, as shown in FIGS. 16 and 17. As described above, the defect may be a subsurface defect or a partially subsurface defect. In addition, the defect may be a surface defect. The portion of the material that is removed may have an area that is equal to or less than about 10 μm by about 10 μm, as described above. As further described above, the area of the portion of the material that is removed may vary depending on, for example, parameters of the electron beam as well as parameters of the light beam. In some embodiments, the material may include a device film. In such an embodiment, the one or more chemicals in combination with electron beam 160 and light beam 150 do not substantially alter an aspect ratio of device features on the substrate as further described above.

Light source 148 may be a laser. However, the light source may be any other appropriate light source known in the art. In general, light sources that are relatively bright at their operating wavelengths may be particularly suitable for use in the systems described herein. One example of an appropriate laser is a Q-switched laser in the 100 mW range. Another appropriate laser may be a Ti-sapphire laser. The light source may also be a single wavelength laser or a multiple wavelength laser. In addition, the light beam may be generated using more than one light source. For example, light from several lasers may be combined into an optical train with a combiner. In another example, different light beams may be generated by different lasers, and the light beam that is delivered to the substrate may vary depending on the material being removed. In this manner, not all of the different light beams may be delivered to the substrate at the same time.

The wavelength of light beam 150 will vary depending on the material that is being removed. For example, depending on the material being removed, the wavelength of light beam 150 is selected such that the light can be absorbed by the material. In this manner, the electron and light delivery subsystem may be configured such that light beam 150 heats a material on the substrate as described above. In addition, the light beam may have one wavelength (e.g., monochromatic light), approximately one wavelength (e.g., near monochromatic light), or more than one wavelength of light (e.g., polychromatic light or broadband light). Examples of appropriate wavelengths include, but are not limited to, about 1054 nm (near infrared), about 527 nm (visible, green), about 350 nm (near ultraviolet), and about 266 nm (ultraviolet). In general, appropriate wavelength(s) may include any wavelength(s) from about 266 nm to about 1054 nm.

If light having different wavelengths is delivered to the substrate at the same time or sequentially, each wavelength may heat a specific material more than it heats others. Therefore, as material is removed from the substrate, the wavelength of the light that is delivered to the substrate may be changed. For example, after a portion of a material on the substrate is removed, a different material formed under the material may be removed using the chemical etching in combination with the electron beam and the light beam, but with different parameters for at least the light beam. In this manner, the electron and light delivery subsystem may be configured such that light beam 150 differentially heats each material with the light beam. In a similar way, when more than one material is being removed from a substrate, parameters of the etch chemistry and/or the electron beam may be changed when different materials are being removed. In this manner, parameters of each component used in the de-layering process may be optimized for removal of the material(s) on the substrate. In addition, parameters of each component used in the de-layering process may be altered to maximize the selectivity of the de-layering process. In particular, the parameters may be altered depending on the composition of the defect, the composition of the material, and in some instances the composition of the substrate. Preferably, the parameters of the etch chemistry, the electron beam, and the light beam used in the de-layering process are optimized to minimize removal of the defect while maximizing removal of the material.

As described further above, light beam 150 preferentially heats the portion of the material on the substrate that is being removed. Heating the material with light beam 150 in the presence of an etch chemistry and electron beam 160 increases the preferential etching of the horizontal surfaces of the portion of the material being removed. In particular, by delivering light beam 150 to a substrate coaxially with electron beam 160, the electron and light delivery subsystem may be configured such that light beam 150 heats a horizontal surface of the material and does not substantially heat a vertical surface of the material. In this manner, electron and light beam assisted chemical etching can be substantially anisotropic. As a result, the de-layering methods described herein provide the ability to remove device films while maintaining the original aspect ratio of the device features or any other three-dimensional features on the substrate, which is critical in defect review and analysis.

A system that includes the electron and light delivery subsystem shown in FIGS. 20 and 21 may also include an analysis subsystem (not shown). The analysis subsystem is configured to measure a characteristic of the defect on the substrate. The characteristic of the defect may include any of those described herein. The characteristic of the defect being measured may determine what analysis is performed on the defect. The analysis subsystem may be configured to perform one of the analysis techniques described herein.

In one embodiment, the electron and light delivery subsystem may be configured to measure a characteristic of the defect using electron beam 160. In this manner, the electron and light delivery subsystem may be configured to function as the analysis subsystem. For example, electron beam 160 that was used for de-layering may also be used to analyze the defect. Parameters of the electron beam used for de-layering may be different than parameters of the electron beam that are used to measure the characteristic of the defect. The parameters of the electron beam may be altered between removal and measurement by altering one or more parameters of the electron and light delivery subsystem. The parameter(s) of the electron and light delivery subsystem may be altered or controlled by a processor (not shown) in some embodiments. The processor may be further configured as described above.

In one embodiment, the electron and light delivery subsystem may be configured to image the defect using a technique such as scanning electron microscopy. The image of the defect may then be used for defect review or to determine characteristics such as lateral dimensions of the defect. In another embodiment, the electron and light delivery subsystem may be used to image the defect as the material is being removed. In this manner, the defect and the de-layering process can be monitored and recorded, which may provide further information about the defect, the material proximate the defect, and the de-layering process. This information may be used to monitor and/or control the de-layering process as described above. In another example, the electron and light delivery subsystem may be configured to determine a composition of the defect using a technique such as ELDX, which is described further above. Once the defect composition has been determined, the de-layering methods described herein may be altered to maximize the selectivity between the defect and the surrounding films.

In other embodiments, light beam 150 may be used to analyze the defect. In this manner, the electron and light delivery subsystem may be configured to analyze the defect using light beam 150 and/or electron beam 160. In one example, light beam 150 may be used to image the defect. The image of the defect may then be used to determine one or more characteristics of the defect such as those described further above. Parameters of the light beam may be changed between removal and analysis as described above. In another embodiment, light beam 150 may be used to image the defect as the material is being removed. In this manner, the defect and the de-layering process can be monitored and recorded, which may provide further information about the defect, the material proximate the defect, and the de-layering process. This information may also be used as described above. In other embodiments, analysis of the defect may be performed using a different light beam (not shown), which may or may not be coaxial with the electron beam.

In another embodiment, the analysis subsystem may include an x-ray analysis system such as those described above or any of those known in the art. In other embodiments, analysis of the defect may be performed using any other analytical technique known in the art. For example, the defect may be analyzed using SIMS, as described further above. The analysis system may be coupled to the system in any manner. For example, the analysis system and the system may be disposed in one housing, coupled by a common processor, a common substrate handler, a common power source, a transmission medium, etc. The embodiment of the electron and light delivery subsystem shown in FIGS. 20 and 21 may be further configured as described herein.

Further modifications and alternative embodiments of various aspects of the invention may be apparent to those skilled in the art in view of this description. For example, methods and systems for measuring a characteristic of a substrate or preparing a substrate for analysis are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for preparing a substrate for analysis, comprising removing a portion of a material on the substrate proximate to a defect using chemical etching in combination with an electron beam, wherein the defect is not substantially altered by said removing, and wherein the portion of the material that is removed proximate to the defect laterally surrounds the defect.

2. The method of claim 1, wherein the defect comprises a subsurface defect or a partially subsurface defect.

3. The method of claim 1, wherein the portion of the material that is removed has an area that is equal to or less than about 10 μm by about 10 μm.

4. The method of claim 1, further comprising removing a portion of an additional material on the substrate proximate to the defect using the chemical etching in combination with the electron beam, wherein the additional material is different than the material, and wherein the additional material is formed under the material.

5. The method of claim 1, further comprising analyzing the defect using the electron beam to determine a characteristic of the defect.

6. The method of claim 1, further comprising analyzing the defect using an x-ray analysis system to determine a characteristic of the defect.

7. The method of claim 1, further comprising analyzing the defect to determine a characteristic of the defect, wherein the characteristic of the defect comprises a composition.

8. The method of claim 1, wherein said chemical etching comprises exposing the substrate to an etch chemistry, and wherein the etch chemistry comprises a fluorine-based chemistry, a chlorine-based chemistry, a bromine-based chemistry, or an oxygen-based chemistry.

9. The method of claim 1, wherein the substrate comprises a product wafer.

10. A method for preparing a substrate for analysis, comprising removing a portion of a material on the substrate proximate to a defect using chemical etching in combination with an electron beam and a light beam, wherein the electron beam is delivered to the substrate coaxially with the light beam, wherein the defect is not substantially altered by said removing, and wherein the portion of the material that is removed proximate to the defect laterally surrounds the defect.

11. The method of claim 10, wherein said removing comprises heating the material with the light beam.

12. The method of claim 10, wherein said removing comprises heating a horizontal surface of the material and not substantially heating a vertical surface of the material.

13. The method of claim 10, wherein the material comprises a device film, and wherein said removing does not substantially alter an aspect ratio of device features on the substrate.

14. The method of claim 10, wherein the defect comprises a subsurface defect or a partially subsurface defect.

15. The method of claim 10, wherein the portion of the material that is removed has an area that is equal to or less than about 10 μm by about 10 μm.

16. The method of claim 10, further comprising analyzing the defect using the electron beam to determine a characteristic of the defect.

17. The method of claim 10, further comprising analyzing the defect using an x-ray analysis system to determine a characteristic of the defect.

18. The method of claim 10, further comprising analyzing the defect to determine a characteristic of the defect, wherein the characteristic of the defect comprises a composition.

19. The method of claim 10, wherein said chemical etching comprises exposing the substrate to an etch chemistry, and wherein the etch chemistry comprises a fluorine-based chemistry, a chlorine-based chemistry, a bromine-based chemistry, or an oxygen-based chemistry.

20. The method of claim 10, further comprising removing a portion of an additional material on the substrate proximate to the defect using the chemical etching in combination with the electron beam and the light beam, wherein the additional material is different than the material, and wherein the additional material is formed under the material.

21. The method of claim 20, wherein said removing the portion of the material and said removing the portion of the additional material comprise differentially heating the material and the additional material with the light beam.

* * * * *